(12) United States Patent
Wang et al.

(10) Patent No.: US 11,191,483 B2
(45) Date of Patent: Dec. 7, 2021

(54) WEARABLE BLOOD PRESSURE MEASUREMENT SYSTEMS

(71) Applicant: Zepp, Inc., Cupertino, CA (US)

(72) Inventors: Rui Wang, Mountain View, CA (US);
Jun Yang, Mountain View, CA (US);
Yurong Xu, Mountain View, CA (US)

(73) Assignee: Zepp, Inc., Cupertino, CA (US)

(*) Notice: Subject to any disclaimer, the term of this patent is extended or adjusted under 35 U.S.C. 154(b) by 585 days.

(21) Appl. No.: 15/478,866

(22) Filed: Apr. 4, 2017

(65) Prior Publication Data

US 2018/0279953 A1    Oct. 4, 2018

(51) Int. Cl.
| | |
|---|---|
| A61B 5/00 | (2006.01) |
| A61B 5/0205 | (2006.01) |
| A61B 5/11 | (2006.01) |
| A61B 5/318 | (2021.01) |
| A61B 5/021 | (2006.01) |
| A61B 5/0533 | (2021.01) |
| A61B 5/024 | (2006.01) |

(52) U.S. Cl.
CPC .......... *A61B 5/6831* (2013.01); *A61B 5/0022* (2013.01); *A61B 5/0205* (2013.01); *A61B 5/1118* (2013.01); *A61B 5/318* (2021.01); *A61B 5/6824* (2013.01); *A61B 5/6826* (2013.01); *A61B 5/021* (2013.01); *A61B 5/02416* (2013.01); *A61B 5/0533* (2013.01); *A61B 2560/0214* (2013.01)

(58) Field of Classification Search
CPC ... A61B 5/6831; A61B 5/0022; A61B 5/0205; A61B 5/0402; A61B 5/1118; A61B 5/6824; A61B 5/6826; A61B 5/021; A61B 5/02416; A61B 5/0533; A61B 2560/0214
See application file for complete search history.

(56) References Cited

U.S. PATENT DOCUMENTS

| | | | |
|---|---|---|---|
| 5,337,750 A | 8/1994 | Walloch | |
| 8,512,240 B1* | 8/2013 | Zuckerman-Stark | ........................ G16H 50/30 600/301 |
| 2003/0176795 A1* | 9/2003 | Harris | ................. A61B 5/02208 600/485 |
| 2004/0193211 A1* | 9/2004 | Voegele | ............... A61B 5/6826 606/205 |
| 2005/0070805 A1* | 3/2005 | Dafni | ................. A61B 5/02007 600/492 |

(Continued)

FOREIGN PATENT DOCUMENTS

WO    WO 2017-109064    *  6/2017

*Primary Examiner* — Lynsey C Eiseman
*Assistant Examiner* — Jessandra F Hough
(74) *Attorney, Agent, or Firm* — Young Basile Hanlon & MacFarlane, P.C.

(57) ABSTRACT

Systems and methods for receiving galvanic skin response data from a galvanic skin response sensor that includes multiple electrodes fastened to a hand of a human; monitoring the galvanic skin response data to determine a time for initiating a Blood Pressure (BP) measurement using a blood pressure measurement cuff worn by the human (e.g., in a continuous or on-demand BP measurement mode); at the determined time, initiating the blood pressure measurement using the blood pressure measurement cuff; receiving blood pressure data for the human that results from the blood pressure measurement; and storing a blood pressure value that is based on the blood pressure data.

19 Claims, 11 Drawing Sheets

(56) References Cited

U.S. PATENT DOCUMENTS

| | | | | |
|---|---|---|---|---|
| 2005/0228297 A1* | 10/2005 | Banet | .................... | A61B 5/021 |
| | | | | 600/485 |
| 2006/0142968 A1* | 6/2006 | Han | .................... | A61B 5/0205 |
| | | | | 702/120 |
| 2008/0081963 A1* | 4/2008 | Naghavi | .............. | A61B 5/6806 |
| | | | | 600/301 |
| 2009/0069720 A1* | 3/2009 | Beck | .................... | A61B 5/4866 |
| | | | | 600/587 |
| 2010/0298652 A1* | 11/2010 | McCombie | .......... | A61B 5/0002 |
| | | | | 600/301 |
| 2015/0099941 A1* | 4/2015 | Tran | .................... | A61B 5/7214 |
| | | | | 600/300 |
| 2015/0327784 A1* | 11/2015 | Lading | ................ | A61B 5/6898 |
| | | | | 600/485 |
| 2017/0243508 A1* | 8/2017 | Cheng | .................... | G09B 5/02 |
| 2018/0028106 A1* | 2/2018 | Leschinsky | .......... | A61B 5/4839 |
| 2019/0175097 A1* | 6/2019 | Cowie | ................. | A61B 5/6826 |

\* cited by examiner

WEARABLE BLOOD PRESSURE MEASUREMENT SYSTEMS

TECHNICAL FIELD

This disclosure relates to wearable blood pressure measurement systems.

BACKGROUND

Wearable devices for fitness monitoring applications are becoming increasingly commonplace. These wearable devices may be used to measure certain vital signals, such as pulse, which may be indicative of heart rate, while also supporting a variety of other applications, such as tracking a user's exercise and fitness progress, check a user's emails or social media accounts, etc. Blood pressure measurement systems are available in hospitals and other controlled medical settings for measuring blood pressure to assess human health.

SUMMARY

Disclosed herein are implementations of wearable blood pressure measurement systems.

In a first aspect, the subject matter described in this specification can be embodied in systems that include a band configured to be worn on a wrist of a human; a wireless communications interface attached to the band; a blood pressure measurement cuff attached to the band; and a galvanic skin response sensor, comprising two electrodes that are configured to be worn on a hand of the human, in which the galvanic skin response sensor is attached to the band.

In a second aspect, the subject matter described in this specification can be embodied in methods that include receiving galvanic skin response data from a galvanic skin response sensor that includes two electrodes fastened to a hand of a human; monitoring the galvanic skin response data to determine a time for initiating a blood pressure measurement using a blood pressure measurement cuff worn by the human; at the determined time, initiating the blood pressure measurement using the blood pressure measurement cuff; receiving blood pressure data for the human that results from the blood pressure measurement; and storing a blood pressure value that is based on the blood pressure data.

In a third aspect, the subject matter described in this specification can be embodied in systems that include a band configured to be worn on a wrist of a human; a battery attached to the band; a wireless communications interface attached to the band; a blood pressure measurement cuff configured to be worn on the wrist or a finger of the human, in which the blood pressure measurement cuff is attached to the band; and a processing apparatus. The processing apparatus may be configured to initiate a blood pressure measurement using the blood pressure measurement cuff; receive blood pressure data for the human that results from the blood pressure measurement; and store a blood pressure value that is based on the blood pressure data.

In a fourth aspect, the subject matter described in this specification can be embodied in systems that include a processor and a memory storing instructions executable by the processor that upon execution by the processor cause the processor to perform operations including receiving galvanic skin response data from a galvanic skin response sensor that includes two electrodes fastened to a hand of a human; monitoring the galvanic skin response data to determine a time for initiating a blood pressure measurement using a blood pressure measurement cuff worn by the human; at the determined time, initiating the blood pressure measurement using the blood pressure measurement cuff; receiving blood pressure data for the human that results from the blood pressure measurement; and storing a blood pressure value that is based on the blood pressure data.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1A:
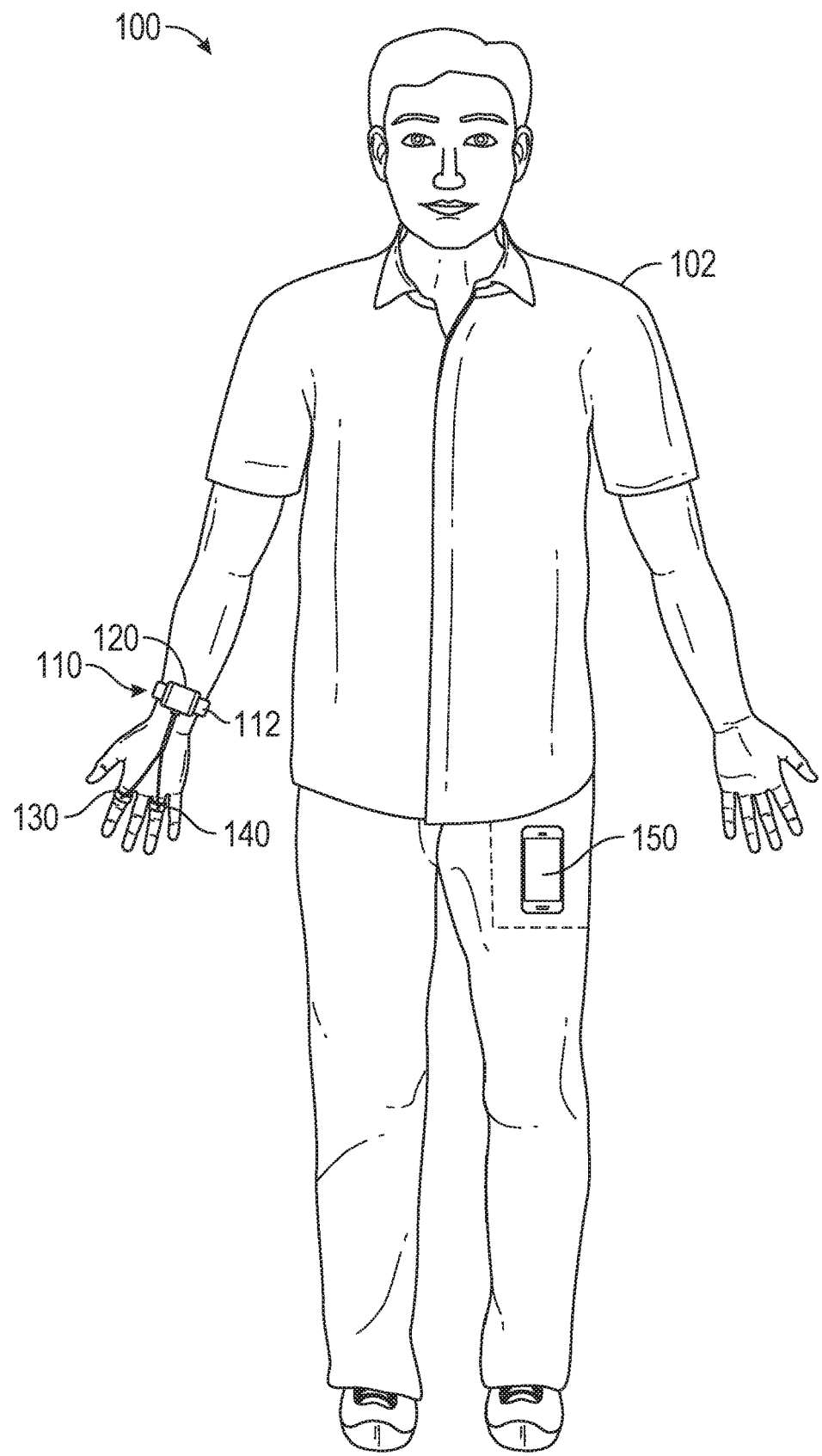
FIG. 1A illustrates an example blood pressure measurement system worn by a human.

Monitoring blood pressure accurately is important for numerous health and fitness applications, such as hypertension management. Inaccurate blood pressure measurements could lead to inappropriate hypertension treatments (e.g., antihypertension medications). Such mistreatment can expose patients to adverse drug effects. Several prerequisites should be satisfied to get accurate blood pressure measurements for health diagnostic purposes. For example, the subject should generally avoid physical activities and moods influencing the blood pressure by avoiding vigorous physical activities 30 minutes before the measurement and sitting calmly for 5 minutes before and during the measurement. During the measurement, the user should be sitting calmly, relaxed, and avoid moving their arms. Currently, an additional person (e.g., a nurse or doctor) check these prerequisites manually.

Methods and systems are described for automatically and objectively evaluating a user's blood pressure measurement prerequisites using wearable sensors. These methods and systems may provide a way to measure a user's blood pressure upon detecting that the prerequisites have been satisfied. In addition to a blood pressure value, a measurement may provide a quality score and/or a calmness score, which may be used for later measurement quality control. The systems may include a device (e.g., a smartwatch) configured to be worn on the wrist of a human with an attached blood pressure measurement cuff (e.g., configured to be worn around a finger of the human or around the wrist) that may be used to perform a blood pressure measurement for the human.

A blood pressure measurement may be timed based a calmness score that is based on a galvanic skin response signal from a galvanic skin response sensor with electrodes fastened to a hand of a human (e.g., fastened with finger cuffs or rings worn by the human). For example, the calmness score may be indicative of a mental state of the human that activate the sympathetic nervous systems (SNS) of the human and causes sweat secretion on the hand. In some implementations, the calmness score may be determined by adding normalized peak amplitudes from the galvanic skin response signal within a window of time and applying a non-linear mapping to the sum to obtain a calmness score in useful range (e.g., from 0 to 100) for comparison and/or combination with other metrics related to the quality of a blood pressure measurement.

In some implementations, information from additional sensors may be used to assess the quality of blood pressure measurement and/or determine the timing of the blood pressure measurement. For example, data from motion sensors (e.g., accelerometers and/or gyroscopes) may be used to determine an activity score that may be indicative of to recent level of exertion by the human subject, which can also impact the quality or diagnostic value of a blood pressure measurement. An activity score may also be mapped to a useful range for comparison and/or combination with other metrics related to the quality of a blood pressure measurement. For example, data from heart rate sensors (e.g., a photoplethysmogram sensor and/or an electrocardiogram sensor) may be used to determine an estimate of heart rate of the human. The heart rate estimate and/or variations in the heart rate estimate over time may be checked against conditions (e.g., a threshold) as an additional check to verify that the human is ready for high quality blood pressure measurement that may be diagnostically useful.

For example, a quality score for a blood pressure measurement may be determined by combining two or more score indicative of the prerequisites for a high quality blood pressure measurements. The quality score may be saved with the associated blood pressure measurement to facilitate selection and or weighting of the blood pressure measurement in later analysis.

Having these blood pressure measurement methods implemented with a wearable device may enable continuous monitoring of a human, without unduly inhibiting quality of life, to opportunistically identify good times for performing blood pressure measurements. Such a system may provide more and/or higher quality blood pressure data over time that can be used to enhance physical evaluation and diagnosis of the human.

For example, the described methods and systems may utilize two types of sensors. A first type of sensor(s) such as a motion sensor (e.g., an accelerometer and/or a gyroscope), a heart rate sensor (e.g., a photoplethysmogram sensor and/or an electrocardiogram sensor), or a combination of these sensors may be used to detect a human's physical activities. A second type of sensor, such as a galvanic skin response sensor, a heart rate sensor (e.g., a photoplethysmogram sensor and/or an electrocardiogram sensor), or a combination of these sensors may be used to detect the human's mental activities. When the prerequisites of blood pressure measurement are met, the system will automatically trigger a blood pressure cuff or similar device to perform blood pressure measurement. For automatically triggered measurements, a quality score and/or a calmness score may be determined for quality control.

To address the goal that the user should avoid vigorous physical activities before the blood pressure measurement, an accelerometer on a smartphone or a smartwatch (depending on which device the user is wearing) may be used to evaluate the intensity of physical activity in a past time window (e.g., the last 5 minutes) and determine an activity score. Higher activity score may indicate the human has avoided vigorous activities and is ready for the measurement (e.g., the activity score may be inversely proportional to a statistic (e.g., an energy, a standard deviation, or and entropy) of the accelerometer signal. To address the goal that the human should be sitting calmly about 5 minutes before the measurement, we use a galvanic skin response sensor on the fingers to evaluate the mental state or calmness of the human. We determine a calmness score from the galvanic skin response signal. A higher calm score may indicate the human is calm and ready for a blood pressure measurement. The system may measure blood pressure on a finger or on a wrist. The measurement quality may be evaluated by determining a quality score. For example, the quality score may be determined from the accelerometer, galvanic skin response, and the pressure sensor readings collected from the human with a wearable device. The quality score may be used to evaluate whether the user is still, calm, and has arm supported during the measurement.

In some implementations, blood pressure measurement procedures can be implemented by a mobile application that runs on the smartwatch or on a smartphone. The mobile application may receive both physical and mental activity data inferred from accelerometer, photoplethysmogram sensor, and galvanic skin response sensor signals. The mobile application may present reminders to a human user to keep still and calm if necessary, and display blood pressure measurement results together with calmness score and BP quality score.

In most implementations described herein, a blood measurement cuff is used to perform the blood pressure measurements. However, alternative methods and tools for blood pressure measurement may be used in conjunction with the described methods for determining a time for performing a blood pressure measurement and/or determining a score indicative of the quality of a blood pressure measurement. For example, pulse transit time methods for blood pressure measurement may be used.

As used herein, the term "processing apparatus" refers to an apparatus including one or more processors that is configured to execute instructions to process data and/or to control peripheral components or devices.

FIG. 1 illustrates an example blood pressure measurement system 100 worn by a human 102. The system 100 includes a wearable device 110 that includes at least one blood pressure cuff for measuring blood pressure of the human 102 wearing the device 110 and one or more sensors for detecting when the prerequisites for a blood pressure measurement are satisfied and/or for estimating the quality of a blood pressure measurement. For example, the wearable device 110 may be equipped with sensors to detect physical activity (e.g., an accelerometer), detect mental status or calmness (e.g., a galvanic skin response sensor), and measure blood pressure.

The wearable device 110 includes a band 112 configured to be worn on a wrist of a human. For example, the band 112 may include a securing mechanism (e.g., a slot and peg mechanism or snap-lock mechanism). The wearable device 110 also includes a processing apparatus 120 (e.g., a smart watch or a smart wristband). The processing apparatus 120 may include a wireless communications interface (e.g., a Bluetooth interface, ZigBee interface, or a WiFi interface) that is attached to the band. The processing apparatus 120 may include a battery that is attached to the band. The wearable device 110 includes a blood pressure measurement cuff 130 attached (e.g., via a wire attached to the processing apparatus 120) to the band 112. In this example, the blood pressure measurement cuff 130 is configured to be worn on a finger (i.e., the index finger) of the human 102. The blood pressure measurement cuff 130 may be controlled by the processing apparatus 120 to apply pressure around the finger and detect associated pressure signals to perform a blood pressure measurement for the human 102.

The system 100 includes a galvanic skin response sensor, including two electrodes that are configured to be worn on a hand of the human. The galvanic skin response sensor is attached to the band 112. For example, an electrode of the galvanic skin response sensor may be part of a GSR cuff 140 that is attached (e.g., via a wire attached to the processing apparatus 120) to the band 112 and configured to be worn on a finger (i.e., the ring finger) of the human 102. A second electrode of the galvanic skin response sensor may worn at a different location on the hand of the human 102. For example, the second electrode may be part of the blood pressure measurement cuff 130 and be configured to be worn on a different finger (i.e., the index finger) of the hand. In some implementations, one or more electrodes of the galvanic skin response sensor may be worn on the wrist of the human 102.

The example system 100 includes a personal computing device 150 (e.g., a smartphone or a tablet). The wearable device 110 may connect to the personal computing device 150 wirelessly. For example, the user may use the personal computing device 150 to setup the wearable device 110 to measure the blood pressure automatically or manually and show their blood pressure history. In some implementations, the personal computing device 150 includes a processing apparatus that receives (e.g., via a wireless communications link) data based on measurements taken by the wearable device 110 and processes the data to determine a time to perform a blood pressure measurement and/or a quality score for a blood pressure measurement. For example, the processing apparatus of the personal computing device may receive galvanic skin response data via transmissions from the wireless communications interface of the processing apparatus 120 attached to the band 112. For example, a processing apparatus of the personal computing device may implement the technique 400 of FIG. 4. For example, a processing apparatus of the personal computing device may implement the technique 700 of FIG. 7.

The system 100 may determine an opportune time to measure blood pressure based on an estimate of mental and/or physical status of the human 102 according to the sensory data from the wearable device 110 and/or her personal computing device 150. Galvanic skin response signals may be detected by the galvanic skin response sensor and used to assess a mental state of the human 102. For example, a calmness score for the human 102 may be determined based on the galvanic skin response signals. For example, the technique 600 of FIG. 6 may be implemented by the processing apparatus 120 or the processing apparatus of the personal computing device 150 to determine a calmness score for the human 102. In some implementations, the wearable apparatus and/or the personal computing device 150 may include a motion sensor (e.g., an accelerometer or a gyroscope) for detecting physical activity of the human 102. Signals from one or more motion sensors may be used to determine an activity score for the human 102. In some implementations, a quality score for a blood pressure measurement may be determined based on a calmness score and an activity score. The system 100 may use a calmness score and/or an activity score to determine a time to measure blood pressure of the human 102 using the blood pressure measurement cuff 130. Blood pressure measurements performed by the system 100 may be stored, displayed, and/or transmitted by the processing apparatus 120 and/or the personal computing device 150.

Figure 1B:
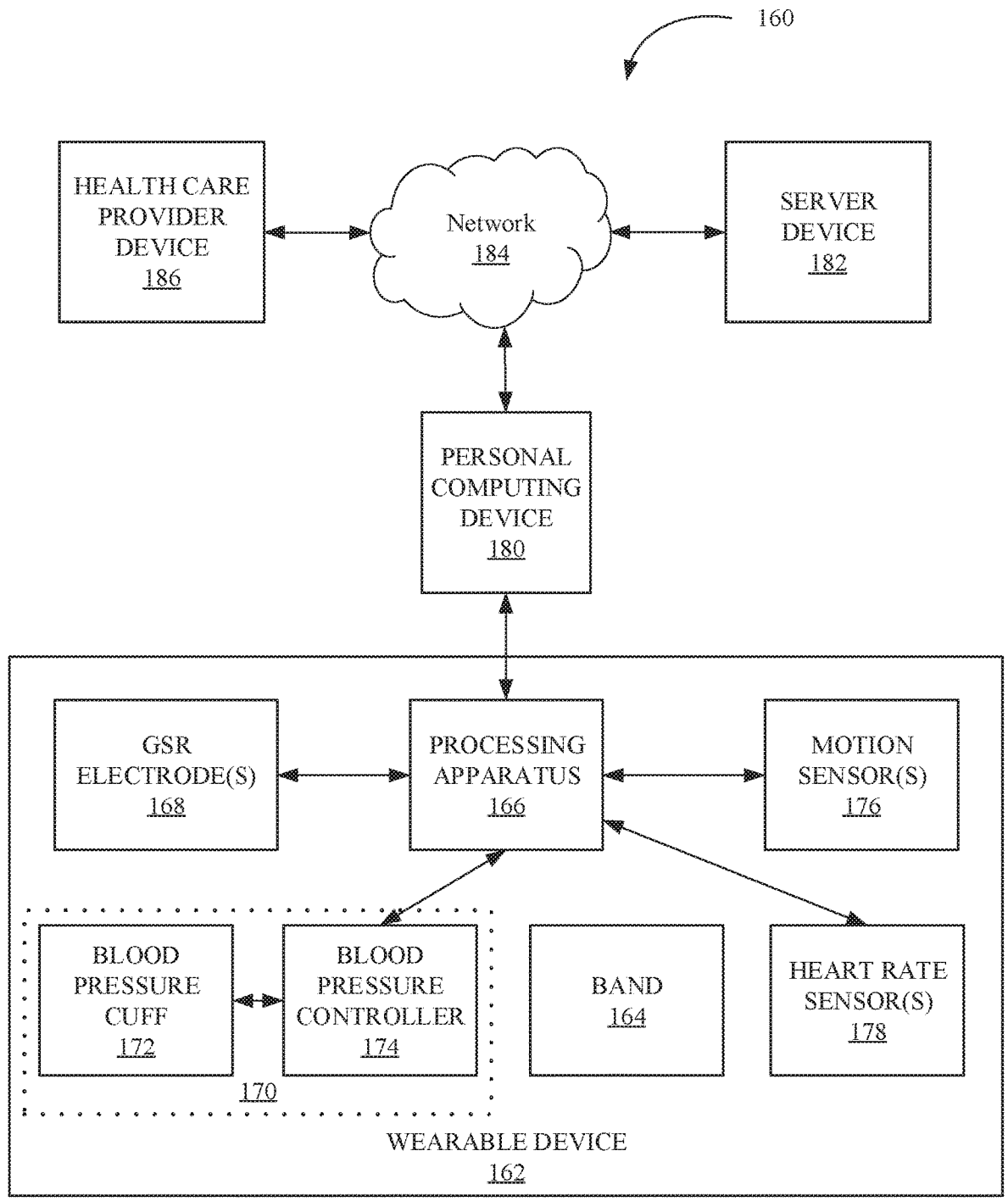
FIG. 1B is block diagram of an example system for blood pressure measurement.

FIG. 1B is block diagram of an example system 160 for blood pressure measurement. The system 160 includes a wearable device 162 configured to gather sensor signals from a human wearing the wearable device 162 and perform blood pressure measurements for the human. The wearable device 162 includes a band 164 configured to be worn on a wrist of the human. The wearable device 162 includes a processing apparatus 166 that interfaces with various sensors of the wearable device 162. The wearable device 162 includes one or more galvanic skin response sensor electrodes 168, a blood pressure sensor 170 (including a blood pressure measurement cuff 172 and a blood pressure controller 174), one or more motion sensors 176, and one or more heart rate sensors 178. For example, all components of the wearable device 162 may be attached (directly or indirectly) to the band 164, such that they are fastened to the human in appropriate locations when the human wears the wearable device 162. The system 160 may also include other devices that receive data based on sensor readings from the wearable device 162 at various stages of processing (e.g., systolic and diastolic blood pressure values, quality scores, or raw sensor readings). Blood pressure data and/or related data indicative of prerequisites for diagnostic blood pressure measurements may be forwarded to a personal computing device 180, a server device 182, and/or a health care provider device 186.

The processing apparatus 166 may include a battery that is attached to the band 164. The processing apparatus 166 may include a wireless communications interface attached to the band 164. For example, the processing apparatus 166 may be the processing apparatus 310 of FIG. 3A. The processing apparatus 166 may be configured to initiate a blood pressure measurement using the blood pressure measurement cuff 172. The processing apparatus 166 may be configured to receive blood pressure data for the human that results from the blood pressure measurement. The processing apparatus 166 may be configured to store a blood pressure value that is based on the blood pressure data. The processing apparatus 166 may be attached to the band 164.

The blood pressure sensor 170 may be configured to use an oscillometric method to perform a blood pressure measurement. The blood pressure measurement cuff 172 may be configured to be worn on the wrist or a finger of the human. For example, the blood pressure measurement cuff 172 may be integrated with the band 164 and worn on the wrist. For example, the blood pressure measurement cuff 172 may be attached to the processing apparatus 166 and worn by the human on a finger of the human. The blood pressure measurement cuff 172 may include a bladder and a pressure sensor. The blood pressure controller 174 may include instructions or other logic for applying and releasing pneumatic pressure in the bladder of the blood pressure measurement cuff 172 during a blood pressure measurement. The blood pressure measurement cuff 172 and the blood pressure controller 174 may be separated or integrated. For example, the blood pressure controller 174 may be include a circuit attached directly to the blood pressure measurement cuff 172.

The wearable device 162 may include a galvanic skin response sensor that includes two electrodes that are configured to be worn on a hand of the human. The galvanic skin response sensor may be attached (directly or indirectly) to the band. For example, the galvanic skin response sensor electrodes 168 may be fastened to respective fingers of the human using cuffs configured to be worn on those fingers. In some implementations, the band 164, when worn by the human, fastens the two electrodes 168 of the galvanic response sensor to opposite sides of the wrist. Signals from the galvanic skin response sensor may be processed to determine a calmness score, which may be indicative of a mental state of the human. For example, the technique 600 of FIG. 6 may be implemented by the processing apparatus 166 or another processing apparatus (e.g., of the personal computing device 180 or the server device 182) to determine a calmness score.

In the example system 160, the motion sensor(s) 176 (e.g., an accelerometer and/or a gyroscope) are attached to the band 164. Readings from the motion sensor(s) may be used to detect activity by the human wearing the wearable device 162. For example, an activity score may be determined based on readings from the motion sensor(s) 176.

Heart rate sensor(s) 178 (e.g., a photoplethysmogram sensor and/or an electrocardiogram sensor) may be used to estimate a heart rate of the human. A heart rate estimate may be used to infer information about physical activity or mental state of a user. For example, an activity score or a calmness score may be based in part on a heart rate estimate. In some implementations, a time for a blood pressure measurement is determined based in part on a heart rate estimate.

Data based on sensor readings may be transmitted (e.g., via a wireless communications interface of the processing apparatus 166) to the personal computing device 180 (e.g., a smartphone, a tablet, a laptop, or wireless router) for processing, use, or forwarding to additional devices that may process or use the data based on the sensor readings. For example, blood pressure values and associated quality scores determined by the processing apparatus 166 may be transmitted to the personal computing device 150. For example, blood pressure values and associated quality scores determined by the processing apparatus 166 may be transmitted (e.g., via the personal computing device 180 and the network 184) to the server device 182 for storage and/or analysis. For example, blood pressure values and associated quality scores determined by the processing apparatus 166 may be transmitted (e.g., via the personal computing device 180 and the network 184) to the health care provider device 186 for storage, analysis, and/or to facilitate the provision of health care services to the human. In some implementations, a sequence of sensor readings are transmitted to the personal computing device 180 for processing by a processing apparatus of the personal computing device 180 to determine a time for measuring blood pressure and/or to determine a quality score for a blood pressure measurement. In some implementations, a sequence of sensor readings are transmitted to the server device 182 for processing by a processing apparatus of the server device 182 to determine a time for measuring blood pressure and/or to determine a quality score for a blood pressure measurement.

Figure 2A:
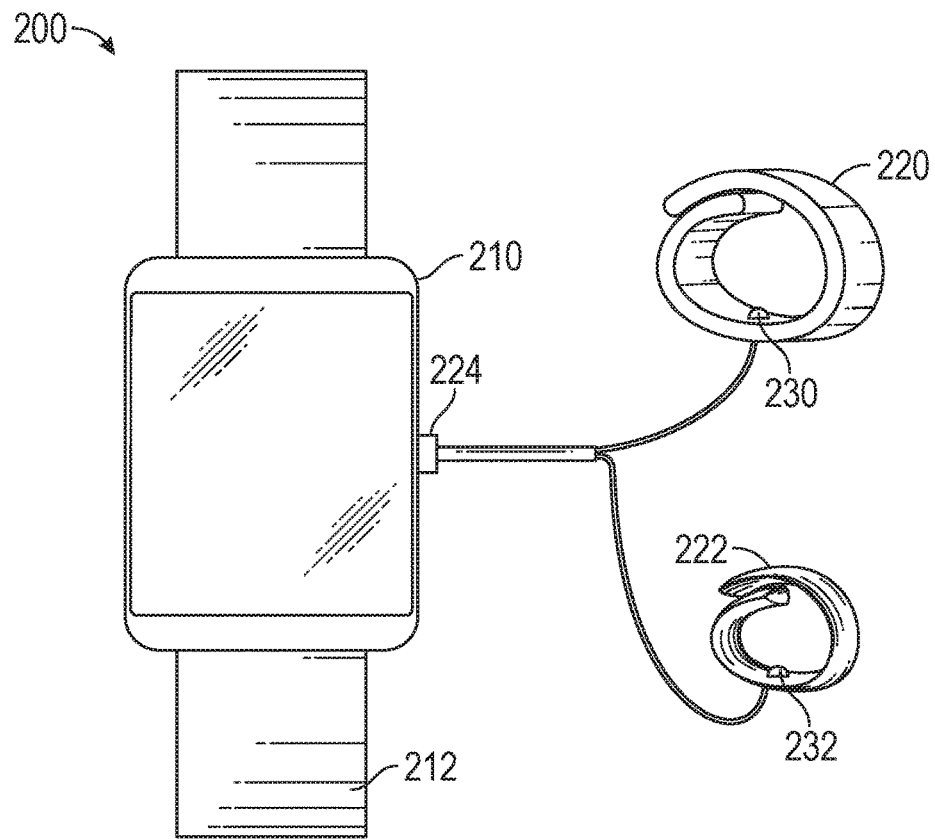
FIG. 2A illustrates an example blood pressure measurement system, including a blood pressure cuff configured to be worn on a finger of a human.

FIG. 2A illustrates an example blood pressure measurement system 200, including a blood pressure cuff 220 configured to be worn on a finger of a human. The system 200 includes a processing apparatus 210 (e.g., a smartwatch) that is attached to a band 212 configured to be worn on a wrist of a human. The processing apparatus 210 may include a wireless communications interface (e.g., the wireless communications interface 318 of FIG. 3A) attached to the band 212. The system 200 includes a blood pressure measurement cuff 220 configured to be worn on a finger of the human. The blood pressure measurement cuff 220 may include an inflatable bladder and a pressure sensor. The blood pressure measurement cuff 220 is attached (e.g., via attachment at cuff interface 224 to the processing apparatus 210) to the band 212. The system 200 includes a second cuff 222 that is configured to be worn on a second finger of the human. The system 200 includes a galvanic skin response sensor, including two electrodes (230 and 232) that are configured to be worn on a hand of the human, in which the galvanic skin response sensor is attached (either directly or indirectly) to the band 212. The first electrode 230 of the galvanic response sensor is attached to the blood pressure measurement cuff 220, which, when worn by the human, fastens the first electrode to a first finger of the human. The second electrode 232 of the galvanic response sensor is attached to the second cuff 222, which, when worn by the human, fastens the second electrode to a second finger of the human. For example, the cuff interface 224 and attached wires may include conductors that are configured to facilitate electronic communication (e.g., of sensor control signals and sensor readings) between the cuffs (220 and 222) and the processing apparatus 210. For example, the processing apparatus 210 may be the processing apparatus 310 of FIG. 3A.

In some implementations, the processing apparatus 210 is a smartwatch that is attached to a pair of detachable BP-GSR finger cuffs (220 and 222). The detachable cuffs are connected to the cuff interface 224 on the smartwatch. The BP-GSR finger cuffs (220 and 222) have two finger cuffs. One cuff 220 is inflatable and may be used to measure blood pressure. The other cuff 222 need not be inflatable. Each finger cuff (220 and 222) has a GSR (galvanic skin response) electrode. For example, a human using the system 200 may choose to wear the cuffs (220 and 222) only when measuring the blood pressure. The smartwatch may be equipped with inertial motion sensors that infer the human's physical activities. The smartwatch may have one or more interfaces to connect to blood pressure cuff 220 and GSR cuffs (220 and 222), with which the smartwatch measures the blood pressure of the human and detects whether the human is calm or not.

In some implementations, the system 200 also includes a smartphone (not shown), which may be used to perform some sensing and data processing functions for blood pressure measurement. For example, various portions of the processing for the techniques described in relation to FIGS. 4-7 may be distributed between a processing apparatus of the smartphone and the processing apparatus 210 per a system design suited to the available resources and an application.

Figure 2B:
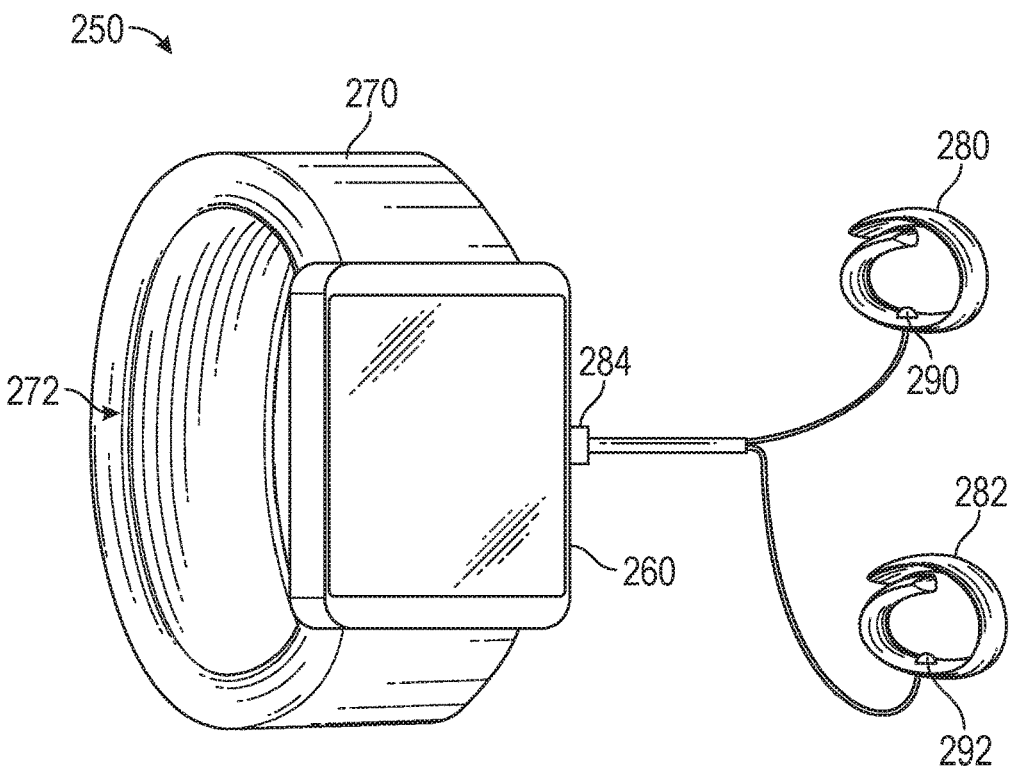
FIG. 2B illustrates an example blood pressure measurement system, including a blood pressure cuff configured to be worn on a wrist of a human.

FIG. 2B illustrates an example blood pressure measurement system 250, including a blood pressure cuff 272 configured to be worn on a wrist of a human. The chief difference between the system 250 and the system 200 is how the blood pressure is measured. System 200 uses a finger cuff 220 to measure blood pressure on a finger, whereas the system 250 uses a wrist cuff 272 to measure blood pressure on a wrist of the human.

The system 200 includes a processing apparatus 260 (e.g., a smartwatch) that is attached to a band 270 configured to be worn on a wrist of a human. The processing apparatus 260 may include a wireless communications interface (e.g., the wireless communications interface 318 of FIG. 3A) attached to the band 270. The system 200 includes a blood pressure measurement cuff 272 configured to be worn on a wrist of the human. The blood pressure measurement cuff 272 may include an inflatable bladder and a pressure sensor. The blood pressure measurement cuff 272 is attached (e.g., directly) to the band 270. The system 200 includes a first cuff 280 that is configured to be worn on a first finger of the human. The system 200 includes a second cuff 282 that is configured to be worn on a second finger of the human. The system 200 includes a galvanic skin response sensor, including two electrodes (290 and 292) that are configured to be worn on a hand of the human. The galvanic skin response sensor may be attached (either directly or indirectly) to the band 270. The first electrode 290 of the galvanic response sensor is attached to the first cuff 280, which, when worn by the human, fastens the first electrode to the first finger of the human. The second electrode 292 of the galvanic response sensor is attached to the second cuff 282, which, when worn by the human, fastens the second electrode to the second finger of the human. For example, the cuff interface 284 and attached wires may include conductors that are configured to facilitate electronic communication (e.g., of sensor control signals and sensor readings) between the cuffs (280 and 282) and the processing apparatus 260. For example, the processing apparatus 210 may be the processing apparatus 310 of FIG. 3A.

In some implementations, the system 250 uses an inflatable watch band (270 and 272) to measure the blood pressure. The watch band (270 and 272) is attached to a similar interface (e.g., the sensor interface 316 of FIG. 3A) as the cuff interface 224 of the system 200. The system 250 may use two ordinary finger cuffs (280 and 2882) to measure galvanic skin response. For example, a human using the system 250 may choose not to wear the cuffs (280 and 282) all the time. However, the system 250 can measure the blood pressure of the human wearing the band 270 without the finger cuffs (280 and 282) on.

For example, the processing apparatus 260 may be a smartwatch that is equipped with inertial motion sensors that infer the human's physical activities. The smartwatch may have one or more interfaces to connect to blood pressure cuff 272 and GSR cuffs (280 and 282), with which the smartwatch measures the blood pressure of the human and detects whether the human is calm or not.

In some implementations, the system 250 also includes a smartphone (not shown), which may be used to perform some sensing and data processing functions for blood pressure measurement. For example, various portions of the processing for the techniques described in relation to FIGS. 4-7 may be distributed between a processing apparatus of the smartphone and the processing apparatus 210 per a system design suited to the available resources and an application.

Figure 3A:
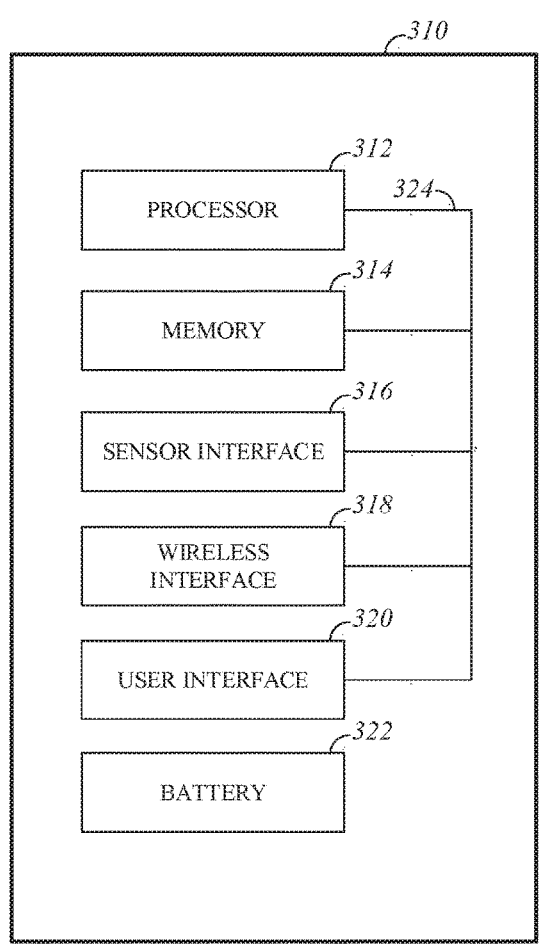
FIG. 3A is a block diagram of an example processing apparatus used for blood pressure measurement.

FIG. 3A is a block diagram of an example processing apparatus used for blood pressure measurement. For example, processing apparatus 310 may be included in a wearable device (e.g., the wearable device 110 or the wearable device 162). The processing apparatus 310 may be used to implement techniques described in this disclosure (e.g., the techniques described in relation to FIGS. 4-7). The example processing apparatus 310 includes a processor 312, a memory 314, a sensor interface 316, a wireless interface 318, a user interface 320, and a battery 322.

The processor 312 may include single or multiple processors each having single or multiple processing cores. Alternatively, the processor 312 may include another type of device, or multiple devices, capable of manipulating or processing data.

The memory 314 may include random access memory device (RAM), flash memory, or any other suitable type of storage device such as a non-transitory computer readable memory. The memory 314 may include executable instructions and data that can be accessed by the processor 312. The memory 314 may include one or more DRAM modules such as double data rate synchronous dynamic random-access memory (DDR SDRAM). The memory 314 may include another type of device, or multiple devices, capable of storing data for retrieval or processing by the processor 312. The processor 312 may access and manipulate data in stored in the memory 314 via a bus 324.

The processing apparatus 310 may include a sensor interface 316, which may receive measurements from one or more sensors (e.g., pressure measurements, galvanic skin response measurements, acceleration measurements, angular rate measurements, photoplethysmogram measurements or electrocardiogram measurements). In some implementations, the sensor interface 316 may implement a serial port protocol (e.g., I2C or SPI) for communications with sensor devices over conductors. In some implementations, the sensor interface 316 may include a wireless interface for communicating with one or more sensor modules via low-power, short-range communications (e.g., using a body area network protocol).

The processing apparatus 310 may include a wireless interface 318, which may enable wireless communications with a personal computing device (e.g., the personal computing device 150 or the personal computing device 180). For example, the wireless interface 318 may be used to forward measurements from sensors and/or information (e.g., blood pressure values and/or quality scores) based on analysis of measurements from sensors. For example, the wireless interface 318 may include a Bluetooth interface, a ZigBee interface, and/or a WiFi interface.

The processing apparatus 310 may include a user interface 320. For example, the user interface 320 may include an LCD display for presenting alerts or other messages to a human wearing a wearable device (e.g., the wearable device 110 or the wearable device 162) or another person assisting that human. For example, the user interface 320 may include button or switch enabling a person to manually turn the processing apparatus 310 on and off.

The processing apparatus 310 may include a battery 322 that powers the processing apparatus 310 and/or its peripherals. For example, the battery 322 may be charged wirelessly or through a micro-USB interface.

Figure 3B:
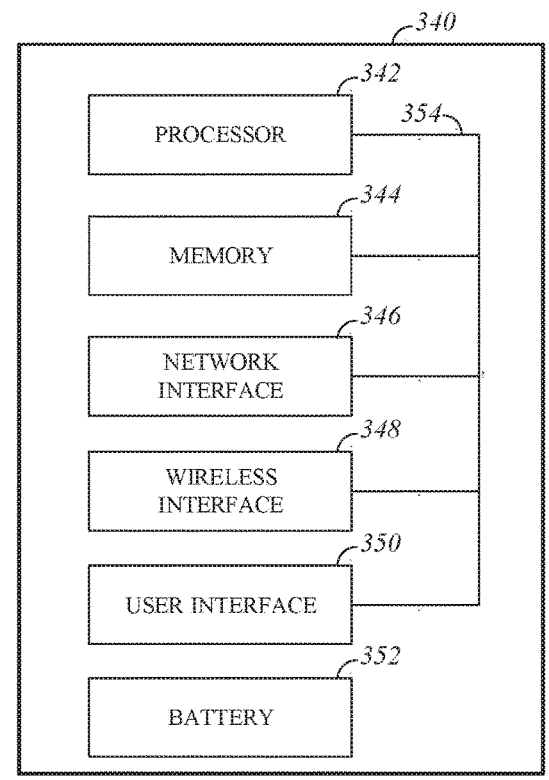
FIG. 3B is a block diagram of an example processing apparatus used for blood pressure measurement.

FIG. 3B is a block diagram of an example processing apparatus used for blood pressure measurement. For example, processing apparatus 340 may be included in a personal computing device (e.g., the personal computing device 150 or the personal computing device 180). The processing apparatus 340 may be used to implement techniques described in this disclosure (e.g., the techniques described in relation to FIGS. 4-7). The example processing apparatus 340 includes a processor 342, a memory 344, a network interface 346, a wireless interface 348, a user interface 350, and a battery 352.

The processor 342 may include single or multiple processors each having single or multiple processing cores. Alternatively, the processor 342 may include another type of device, or multiple devices, capable of manipulating or processing data.

The memory 344 may include random access memory device (RAM), flash memory, a read-only memory device (ROM), an optical disc, a magnetic disc, or any other suitable type of storage device such as a non-transitory computer readable memory. The memory 344 may include executable instructions and data that can be accessed by the processor 342. The memory 344 may include one or more DRAM modules such as double data rate synchronous dynamic random-access memory (DDR SDRAM). The memory 344 may include another type of device, or multiple devices, capable of storing data for retrieval or processing by the processor 342. The processor 342 may access and manipulate data in stored in the memory 344 via a bus 354.

The processing apparatus 340 may include a network interface 346, which may be used to transmit and receive data via a wired and/or wireless computing network (e.g., a cellular data network, a WiFi wireless LAN, an Ethernet LAN, and/or a WAN, such as the Internet). In some implementations, the network interface 346 may implement a network protocol (e.g., IPv4 or IPv6) for communications with other computing devices via a network.

The processing apparatus 340 may include a wireless interface 348, which may enable wireless communications with a peripheral device (e.g., the wearable device 110 or the wearable device 162). For example, the wireless interface 348 may be used to receive blood pressure data for a human that results from a blood pressure measurement, receive galvanic skin response data from a galvanic skin response sensor, receive motion data from a motion sensor, and/or receive heart rate data from a heart rate sensor of a wearable device (e.g., the wearable device 110 or the wearable device 162). In some implementations, the wireless interface 348 may be used to receive information (e.g., blood pressure values, calmness scores, activity scores, heart rate estimates, or quality scores) that is based on analysis of data from sensors of a wearable device. In some implementations, the wireless interface 348 may be used to transmit commands or results (e.g., an indication of a determined time for a blood pressure measurement) to a wearable device (e.g., the wearable device 110 or the wearable device 162). For example, the wireless interface 348 may include a Bluetooth interface, a ZigBee interface, and/or a WiFi interface.

The processing apparatus 340 may include a user interface 350. For example, the user interface 350 may include a touchscreen display for presenting blood pressure values, quality scores, or other messages to a human wearing a wearable device (e.g., the wearable device 110 or the wearable device 162) or another person assisting that human and detecting control gestures by a user. For example, the user interface 350 may include buttons or switches enabling a person to manually turn the processing apparatus on and off, adjust sound volume, etc. In some implementations, the user interface 350 may include a LCD display or CRT monitor for presenting blood pressure values, quality scores, or other messages to a human wearing a wearable device (e.g., the wearable device 110 or the wearable device 162) or another person assisting that human and detecting control gestures by a user. In some implementations, the user interface 350 may include a keyboard, mouse, trackpad, and/or microphone for receiving user input.

The processing apparatus 340 may include a battery 352 that powers the processing apparatus and/or its peripherals. For example, the battery 352 may be charged wirelessly, through a micro-USB interface, or through an AC (alternating current) adapter cable.

Figure 3C:
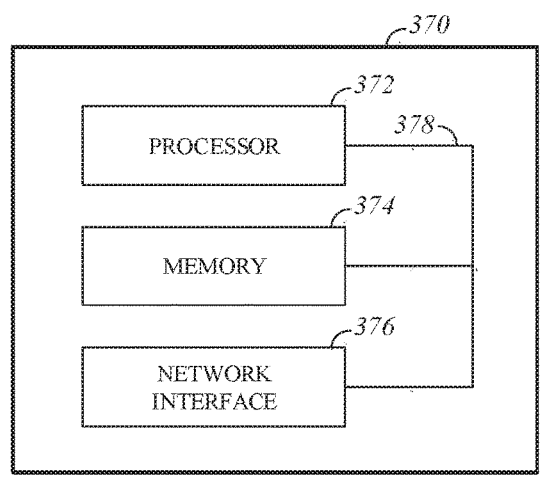
FIG. 3C is a block diagram of an example processing apparatus used for blood pressure measurement.

FIG. 3C is a block diagram of an example processing apparatus used for blood pressure measurement. For example, processing apparatus 370 may be included in a server device (e.g., the server device 182). The processing apparatus 370 may be used to implement techniques described in this disclosure (e.g., the techniques described in relation to FIGS. 4-7). The example processing apparatus 370 includes a processor 372, a memory 374, and a network interface 376.

The processor 372 may include single or multiple processors each having single or multiple processing cores. Alternatively, the processor 372 may include another type of device, or multiple devices, capable of manipulating or processing data.

The memory 374 may include random access memory device (RAM), flash memory, a read-only memory device (ROM), an optical disc, a magnetic disc, or any other suitable type of storage device such as a non-transitory computer readable memory. The memory 374 may include executable instructions and data that can be accessed by the processor 372. The memory 374 may include one or more DRAM modules such as double data rate synchronous dynamic random-access memory (DDR SDRAM). The memory 374 may include another type of device, or multiple devices, capable of storing data for retrieval or processing by the processor 372. For example, the memory 374 can be distributed across multiple machines or devices such as network-based memory or memory in multiple machines performing operations that can be described herein as being performed using a single computing device for ease of explanation. The processor 372 may access and manipulate data in stored in the memory 374 via a bus 378 or via computing network communications (e.g., where the memory includes a database server in separated from the processor 372 by a computing network).

The processing apparatus 370 may include a network interface 376, which may be used to transmit and receive data via a wired and/or wireless computing network (e.g., a cellular data network, a WiFi wireless LAN, an Ethernet LAN, and/or a WAN, such as the Internet). In some implementations, the network interface 376 may implement a network protocols (e.g., IPv4 or IPv6) for communications with other computing devices via a network. For example, blood pressure data for a human that results from a blood pressure measurement made with a blood pressure sensor (e.g., the blood pressure sensor 170) may be received by the processing apparatus 370 via the network interface 376. For example, galvanic skin response data from a galvanic skin response sensor (e.g., including the galvanic skin response sensor electrode(s) 168) may be received by the processing apparatus 370 via the network interface 376. For example, motion data from a motion sensor (e.g., the motion sensor(s) 176) may be received by the processing apparatus 370 via the network interface 376. For example, heart rate data from a heart rate sensor (e.g., the heart rate sensor(s) 178) may be received by the processing apparatus 370 via the network interface 376. In some implementations, the network interface 376 may be used to transmit commands or results (e.g., an indication of a determined time for a blood pressure measurement) to a wearable device (e.g., the wearable device 110 or the wearable device 162). For example, information (e.g., a blood pressure value, a quality score, a calmness score, an activity score, or a heart rate estimate) indicating a blood pressure or associated quality of a measurement may be transmitted by the processing apparatus 370 via the network interface 376 to another device registered to receive blood pressure values for the human (e.g., the health care provider device 186, the personal computing device 180, and/or the wearable device 162.

Figure 4:
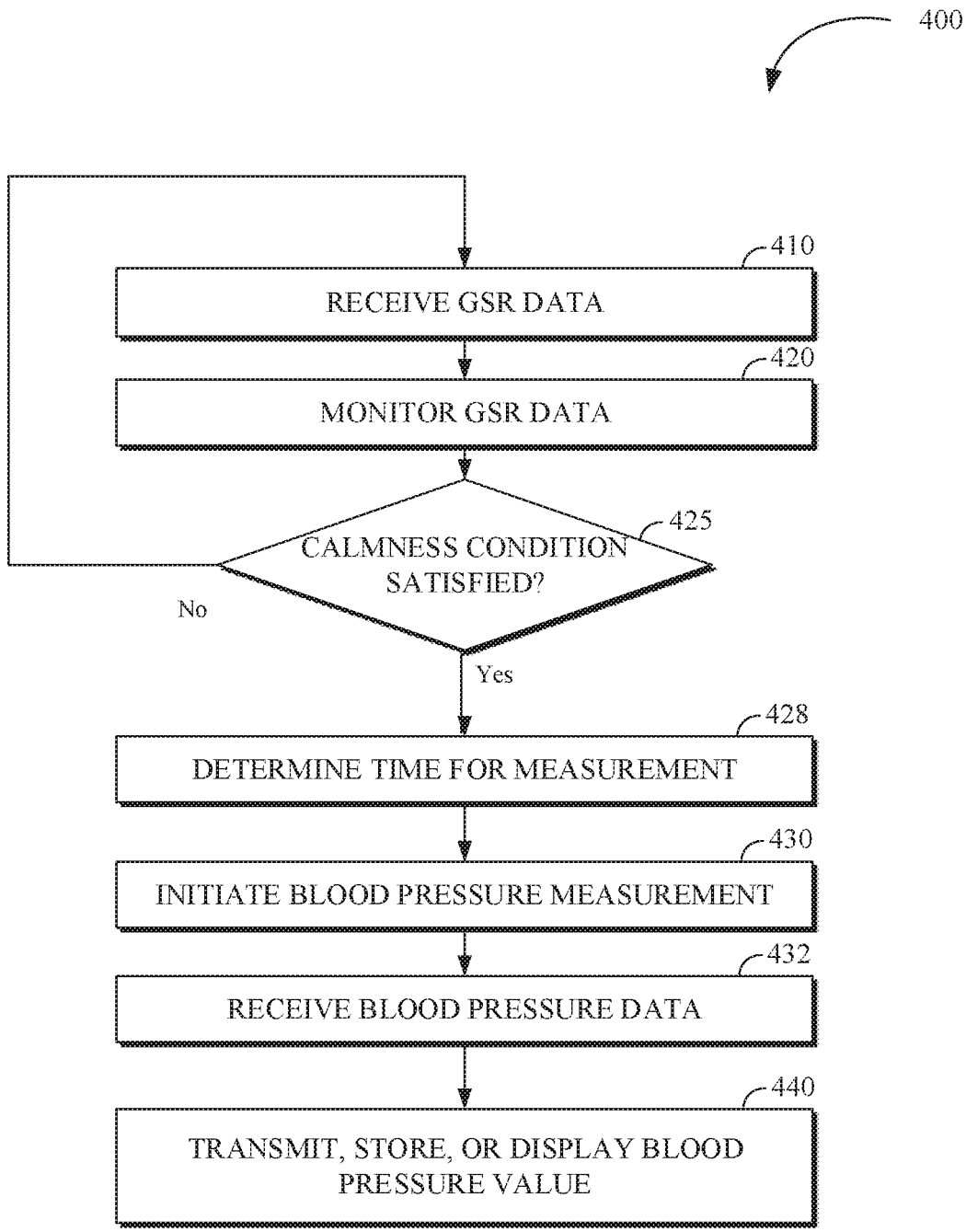
FIG. 4 is a flowchart of an example technique for blood pressure measurement.

FIG. 4 is a flowchart of an example technique 400 for blood pressure measurement. The technique 400 includes receiving 410 galvanic skin response data from a galvanic skin response sensor; monitoring 420 the galvanic skin response data to determine 428 a time for initiating 430 a blood pressure measurement, at the determined 428 time, initiating 430 the blood pressure measurement; receiving 432 blood pressure data for a human that results from the blood pressure measurement; and transmitting, storing, or displaying 440 a blood pressure value that is based on the blood pressure data. For example, the technique 400 may be implemented by a processing apparatus (e.g., the processing apparatuses 310, 340, and 370) that is incorporated in or (directly or indirectly) in communication with a wearable device (e.g., the wearable device 110 or the wearable device 162) worn by the human and configured to perform the blood pressure measurement. In some implementations, the technique 400 may be applied repeatedly or continuously while the wearable device is worn by the human to monitor prerequisites for high quality blood pressure measurements and opportunistically perform blood pressure measurements when conditions are good, which may provide a greater number of high quality blood pressure measurements for the human and enhance health tracking and medical diagnosis of the human.

The example technique 400 includes receiving 410 galvanic skin response data from a galvanic skin response sensor. The galvanic skin response sensor may include two electrodes fastened to a hand of a human. For example, galvanic skin response data may be received 410 via conductors that connect a GSR cuff (e.g., the GSR cuff 140), which includes an electrode fastened to a finger of the human, to a processing apparatus (e.g., the processing apparatus 310). For example, galvanic skin response data may be received 410 via wireless communications (e.g., using Bluetooth, ZigBee, or WiFi protocols) from a wearable device (e.g., the wearable device 110 or the wearable device 162), which includes two or more electrodes fastened to the human, to a processing apparatus (e.g., the processing apparatus 340). For example, galvanic skin response data may be received 410 by a processing apparatus (e.g., the processing apparatus 370) via network communications (e.g., using IPv4 or IPv6 protocols) through a network interface (e.g., the network interface 376). The received 410 blood pressure data may be raw measurements or they may be partially processed measurements (e.g., measurements that have been filtered to suppress noise components in a signal).

The example technique 400 includes monitoring 420 the galvanic skin response data to determine a time for initiating a blood pressure measurement using a blood pressure measurement cuff worn by the human. Monitoring 420 the galvanic skin response data may include determining a calmness score for the human based on the galvanic skin response data corresponding to a galvanic skin response signal within a sliding window of time. For example, the technique 600 of FIG. 6 may be used to determine the calmness score. In some implementations, a calmness score is determined periodically (e.g., once per minute) to monitor 420 the galvanic skin response data for signs that the mental state of the human is conducive to diagnostically useful blood pressure measurement.

Monitoring 420 the galvanic skin response data may include checking whether a calmness condition is satisfied. For example, monitoring 420 the galvanic skin response data may include comparing the calmness score to a threshold to assess a calmness condition. For example, calmness scores may be determined using a non-linear mapping to a scale from 0 to 100, where 100 corresponds a calm state highly conducive to blood pressure measurement and 0 corresponds to an extremely agitated mental state that could significantly impair diagnosis based on a blood pressure measurement. A threshold in this range (e.g., 50 or 75) may be used to decide when the mental state of the human is good (calm) enough to proceed with a blood pressure measurement.

If (at operation 425) the calmness condition is not satisfied, then a blood pressure measurement is not scheduled and instead a system implementing the technique 400 waits to receive 410 more galvanic skin response data for the human and continues monitoring 420 the galvanic skin response data.

If (at operation 425) the calmness condition is satisfied (e.g., when the most recent calmness score exceeds a threshold), then a time for the next blood pressure measurement is determined 428. For example, the technique 400 may include, responsive at least in part to the calmness score satisfying a calmness condition, determining 428 the time for a blood pressure measurement to be a current or upcoming time. In some implementations, an activity score may be determined based on the motion data, and the blood pressure measurement may be initiated 430 responsive at least in part to the activity score satisfying a condition (e.g., the activity score exceeding a threshold).

The example technique 400 includes, at the determined 428 time, initiating 430 a blood pressure measurement using a blood pressure measurement cuff worn by the human. For example, the blood pressure measurement may be initiated 430 by sending a command to blood pressure cuff. For example, the processing apparatus 310 may initiate 430 a blood pressure measurement by sending a command via the sensor interface 316. For example, the processing apparatus 340 may initiate 430 a blood pressure measurement by sending a command via the wireless interface 348 through a wireless communications link with a wearable device that includes the blood pressure cuff. For example, the processing apparatus 370 may initiate 430 a blood pressure measurement by sending a command via the network interface 376 through a communications link with a wearable device that includes the blood pressure cuff. For example, the processing apparatus 166 may initiate 430 a blood pressure measurement by sending a command via the blood pressure controller 174 to the blood pressure cuff 172.

The example technique 400 includes receiving 432 blood pressure data for the human that results from the blood pressure measurement. For example, blood pressure data may be received 432 via conductors that connect a blood pressure measurement cuff (e.g., the blood pressure measurement cuff 130) to a processing apparatus (e.g., the processing apparatus 310). For example, the blood pressure data may be received 432 via wireless communications (e.g., using Bluetooth, ZigBee, or WiFi protocols) from a wearable device (e.g., the wearable device 110 or the wearable device 162) to a processing apparatus (e.g., the processing apparatus 340). For example, blood pressure data may be received 432 by a processing apparatus (e.g., the processing apparatus 370) via network communications (e.g., using IPv4 or IPv6 protocols) through a network interface (e.g., the network interface 376). The received 432 blood pressure data may be a sequence of raw pressure readings (e.g., in units of millimeters of mercury) or they may be partially processed (e.g., readings that have been filtered to suppress noise components in a signal). In some implementations, the received 432 blood pressure data may be a systolic blood pressure value and/or a diastolic blood pressure value.

The example technique 400 includes transmitting, storing, or displaying 440 a blood pressure value that is based on the blood pressure data. For example, the blood pressure value may be a systolic blood pressure estimate and/or a diastolic blood pressure estimate that are determined by applying an oscillometric analysis to the received blood pressure data. For example, the blood pressure value may be transmitted 440 via a communications interface (e.g., the wireless interface 318, the wireless interface 348, the network interface 346, or the network interface 376) of a processing apparatus implementing the technique 400. For example, the blood pressure value may be stored 440 in memory (e.g., the memory 314, the memory 344, or the memory 374) of a processing apparatus implementing the technique 400. For example, the blood pressure value may be displayed 440 in a user interface (e.g., the user interface 320 or the user interface 350) of a processing apparatus implementing the technique 400.

In some implementations, technique 400 may be applied to monitor blood pressure measurement prerequisites continuously over a long period of time while the wearable device is being worn. For example, continuous monitoring may increase the chances of collecting high quality blood pressure measurement and/or increase the number of quality blood pressure measurements collected and logged for medical diagnostic purposes. In some implementations, technique 400 may be applied to monitor blood pressure measurement prerequisites episodically within a short time frame in response to a triggering event (e.g., a measurement command issued through a user interface of a wearable device or a personal computing device), which may conserve power and/or memory.

The example technique 400 may be augmented with additional conditions for scheduling a blood pressure measurement. In some implementations, additional conditions (e.g., an activity condition and/or a heart rate condition) for a blood pressure may be checked in conjunction with the calmness condition to schedule a blood pressure measurement. For example, motion data may be received from a motion sensor (e.g., a motion sensor that is attached to a device worn by the human) and the motion data may be monitored to determine the time for initiating a blood pressure measurement using a blood pressure measurement cuff worn by the human. In some implementations, monitoring the motion data to determine the time includes determining an activity score based on the motion data corresponding to a motion signal within a sliding window of time; comparing the activity score to an activity threshold to assess an activity condition; and responsive at least in part to the activity score satisfying the activity condition, determining the time to be a current or upcoming time.

For example, the activity score may be determined based on a Metabolic Equivalent of Task (MET) algorithm. Readings from one or more motion sensors (e.g., accelerometers and/or gyroscopes) on wearable device (e.g., a smartwatch) and/or on a personal computing device (e.g., a smartphone) may be used to infer a recent energy expenditure by a human wearing or carrying the motion sensor(s). The MET may be determined based on the human's energy expenditure during a recent period (e.g., the last 5 minutes) and the human's body weight. In some implementations, lower METs are associated with higher activity scores, such that a high activity score may be indicative of readiness for a diagnostically useful blood pressure measurement. For example, the activity score may be inversely proportional to the MET. The determination of the activity score can be implemented as sliding window based movement detector (e.g., shifting one minute between consecutive activity score determinations) to check that a low MET score is achieved before a blood pressure measurement is initiated.

For example, the technique 400 may be augmented to include determining an estimate of heart rate for the human based on sensor data from at least one of the sensors from a group including a photoplethysmogram sensor and an electrocardiogram sensor, where the at least one sensors are worn by the human. The technique 400 may be further augmented to include comparing the estimate of heart rate to a heart rate threshold to assess a heart rate condition; and responsive at least in part to the estimate of heart rate satisfying the third condition, determining the time for the blood pressure measurement to be a current or upcoming time.

Figure 5A:
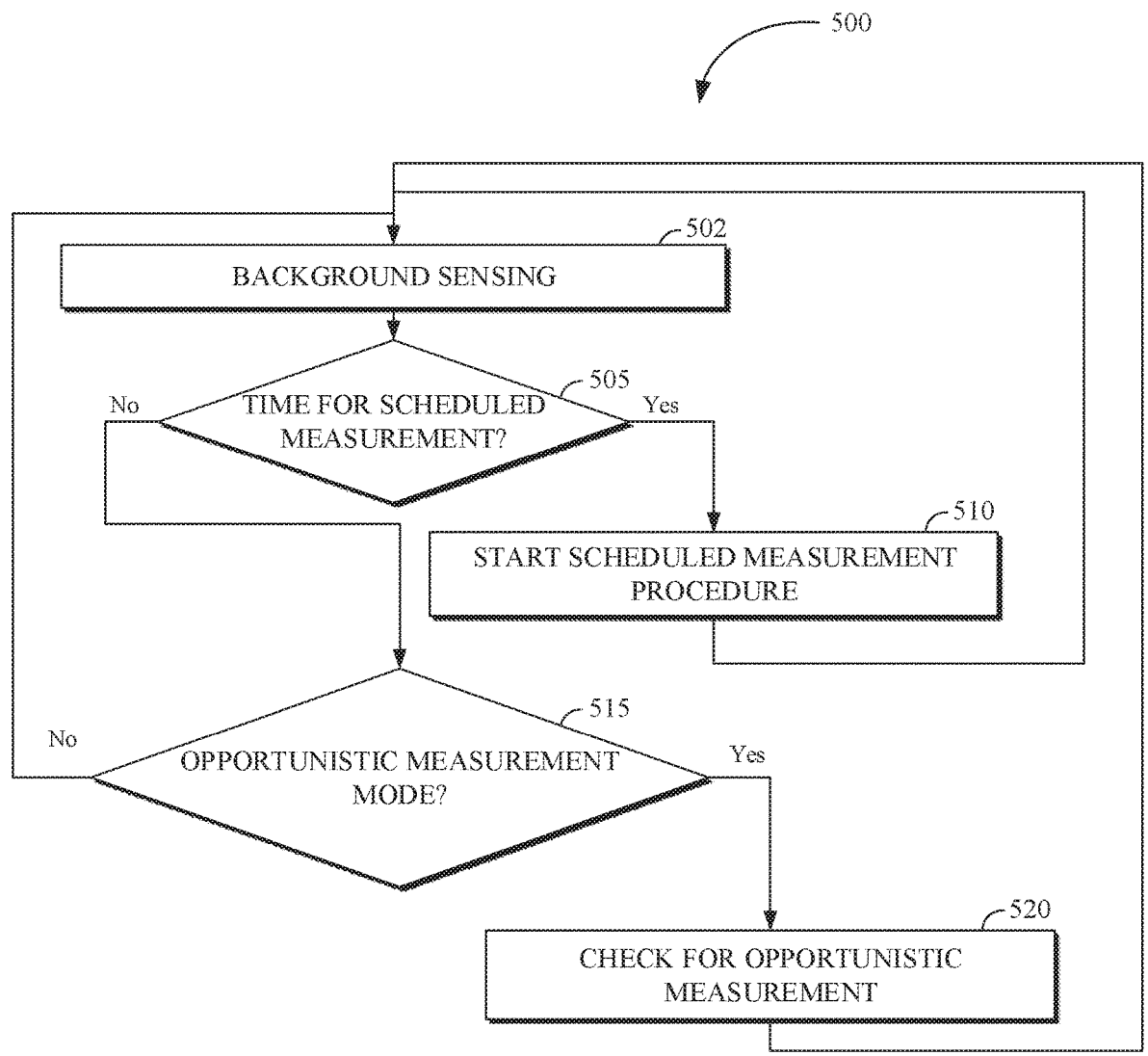
FIG. 5A is a flowchart of an example technique for scheduling a blood pressure measurement.

FIG. 5A is a flowchart of an example technique 500 for scheduling a blood pressure measurement. The example technique 500 includes background sensing 502; at scheduled times, starting 510 a scheduled blood pressure measurement procedure; and, if an opportunistic blood pressure measurement mode is set, checking 520 if there is currently an opportunity for a high quality blood pressure measurement. For example, the technique 500 may be implemented by a processing apparatus (e.g., the processing apparatuses 310, 340, and 370) that is incorporated in or (directly or indirectly) in communication with a wearable device (e.g., the wearable device 110 or the wearable device 162) worn by the human and configured to perform the blood pressure measurement. In some implementations, the technique 500 may be applied repeatedly or continuously while the wearable device is worn by the human to monitor sensor data to detect opportunities for high quality blood pressure measurements and opportunistically perform blood pressure measurements when conditions are good, which may provide a greater number of high quality blood pressure measurements for the human and enhance health tracking and medical diagnosis of the human.

A user (e.g., a human who wears a wearable device that includes a blood pressure measurement cuff) may setup a blood pressure measurement plan on a personal computing device (e.g., a smartphone or tablet). Some medical professionals recommend to measure blood pressure twice a day (e.g., in the morning and late afternoon) at about the same times every day. The user may setup when they want to measure their blood pressure during the morning and late afternoon. The user may also setup how often they want to measure their blood pressure during the day. A system implementing the technique 500 may automatically start the measurement procedures based on the user's setup.

In background sensing 502, a blood pressure measurement system (e.g., the system 100, the system 160, the system 200, or the system 250) continuously collect motion data, GSR data, and/or heartrate data. The blood pressure measurement system triggers alarms for scheduled measurements and opportunistic measurements according to the user's settings. Once an alarm is triggered, the system may check 505 whether it should perform a scheduled measurement or, if not, check 515 whether it is configured to perform opportunistic measurements. For example, the technique 530 of FIG. 5B may be implemented to start 510 a scheduled measurement procedure. For example, the technique 550 of FIG. 5C may be implemented to check 520 for opportunistic measurements.

Figure 5B:
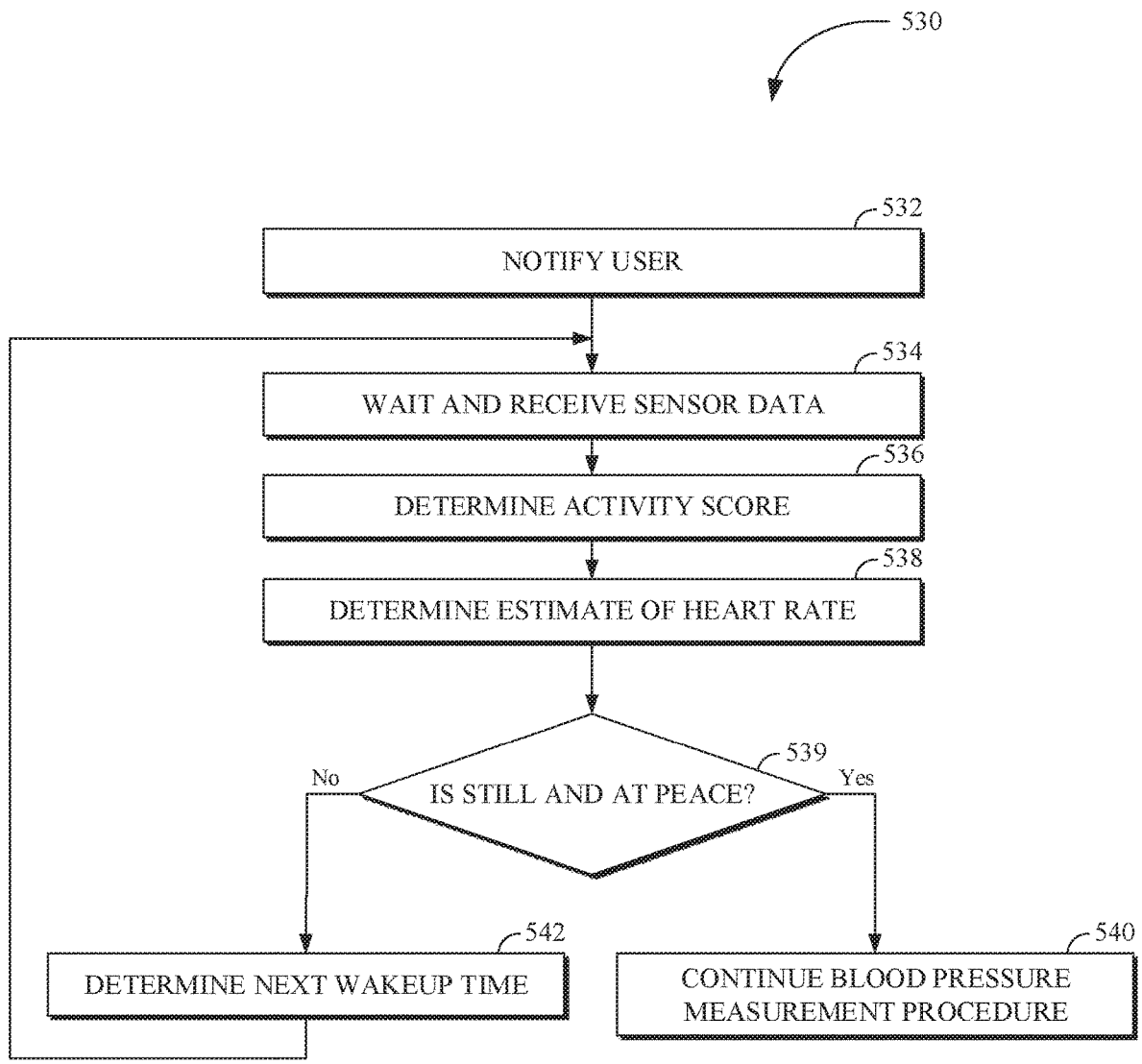
FIG. 5B is a flowchart of an example technique for performing a scheduled blood pressure measurement.

FIG. 5B is a flowchart of an example technique 530 for performing a scheduled blood pressure measurement. The example technique 500 includes notifying 532 a user; waiting and receiving 534 sensor data; determining 536 an activity score based on the sensor data; and determining 538 an estimate of heart rate based on the sensor data. If (at operation 539), based on the activity score and the estimate of heart rate, the human is still and at peace, then the blood pressure measurement procedure continues 540. Otherwise (at operation 539), a next wakeup time is determined 542 and the procedure is restarted by waiting for and receiving 534 sensor data. For example, the technique 530 may be implemented by a processing apparatus (e.g., the processing apparatuses 310, 340, and 370) that is incorporated in or (directly or indirectly) in communication with a wearable device (e.g., the wearable device 110 or the wearable device 162) worn by the human and configured to perform the blood pressure measurement.

A blood pressure measurement system (e.g., the system 100, the system 160, the system 200, or the system 250) implementing the technique 530 first notifies 532 the human about the upcoming scheduled measurement via a user interface (e.g., the user interface 320 or the user interface 350) prior to (e.g., 30 minutes before) the scheduled time and instructs the human to avoid vigorous physical activities in preparation for the blood pressure measurement. The system waits for a short period (e.g., 5 minutes) while keep collecting sensor data (e.g., motion data from an accelerometer and/or heart rate data from a photoplethysmogram sensor) after the scheduled time.

The activity score may be determined 536 based on the Metabolic Equivalent of Task (MET). One or more motion sensors (e.g., accelerometers and/or gyroscopes) on wearable device (e.g., a smartwatch) and/or on a personal computing device (e.g., a smartphone) may be used to infer a recent energy expenditure by a human wearing or carrying the motion sensor(s). The MET may be computed based on the human's energy expenditure during a recent period (e.g., the last 5 minutes) and the human's body weight. In some implementations, lower METs are associated with higher activity scores, such that a high activity score may be indicative of readiness for a diagnostically useful blood pressure measurement. The determination 536 of the activity score can be implemented as sliding window based movement detector (e.g., shifting one minute between consecutive activity score determinations) to confirm that a low MET score is achieved before a blood pressure measurement is taken.

An estimate of heart rate for the human may also be determined 538. Suppose the human has achieved a low MET score within a few minutes, but there heart rate is still elevated due to earlier activity or for some other reason, such as mental distress. For example, data from a photoplethysmogram sensor can be used to measure heart rate of the human to confirm the human is at peace and reduce false alarms.

If (at operation 539) the activity score and the estimate of heart rate both indicate that the human is still and at peace and ready to have their blood pressure measured, the measurement continues 540. For example, the technique 570 of FIG. 5D may be implemented to continue 540 the blood pressure measurement procedure. Otherwise, the next wakeup time may be determined 542 based on the activity data. For example, a sliding window approach may be used to estimate a time in the future that the activity score might reach a threshold required to continue 540 the blood pressure measurement.

Figure 5C:
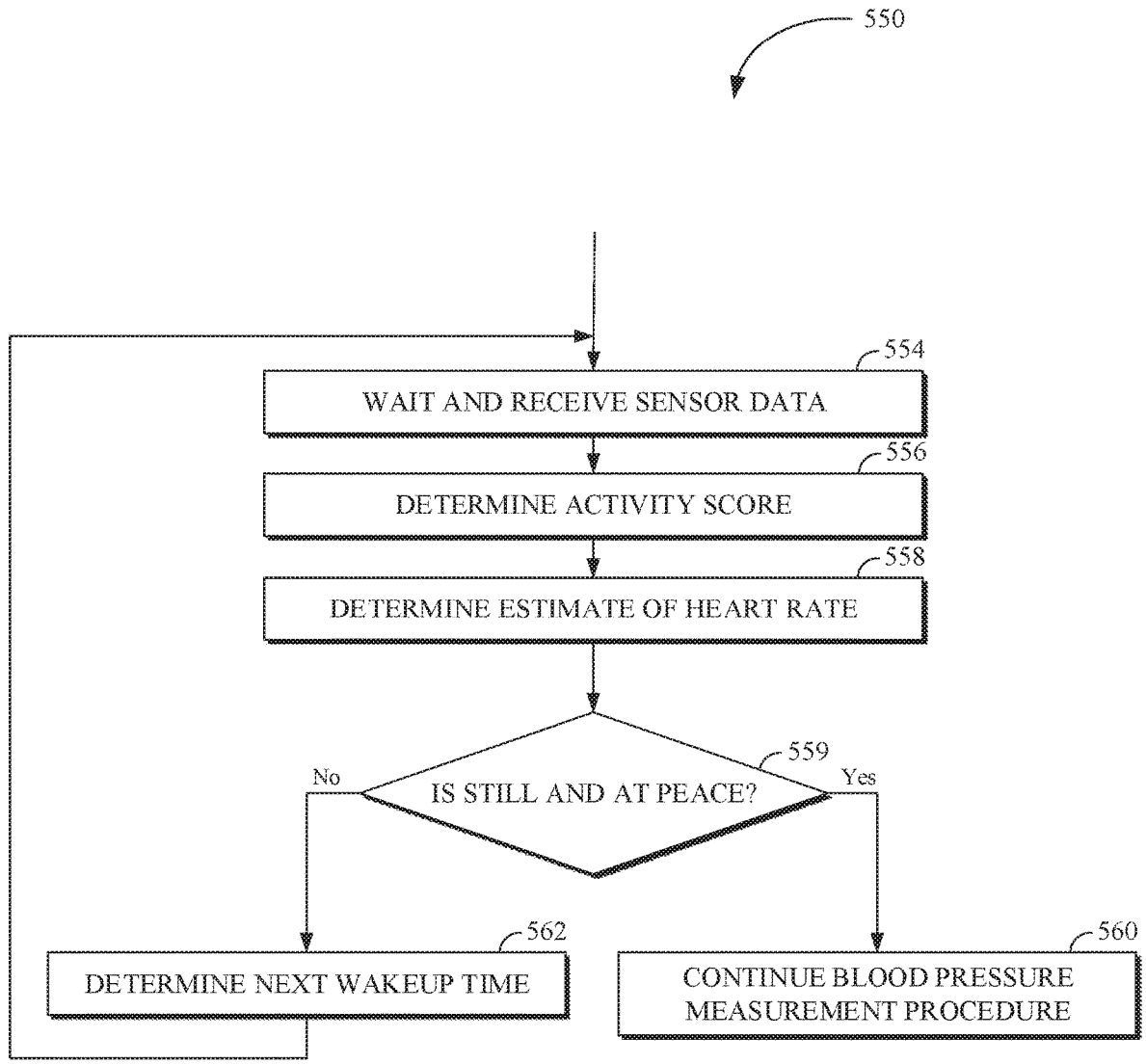
FIG. 5C is a flowchart of an example technique for performing an opportunistic blood pressure measurement.

FIG. 5C is a flowchart of an example technique 550 for performing an opportunistic blood pressure measurement. The example technique 550 includes waiting and receiving 554 sensor data; determining 556 an activity score based on the sensor data; and determining 558 an estimate of heart rate based on the sensor data. If (at operation 559), based on the activity score and the estimate of heart rate, the human is still and at peace, then the blood pressure measurement procedure continues 560. Otherwise (at operation 559), a next wakeup time is determined 562 and the procedure is restarted by waiting for and receiving 554 sensor data. For example, the technique 550 may be implemented by a processing apparatus (e.g., the processing apparatuses 310, 340, and 370) that is incorporated in or (directly or indirectly) in communication with a wearable device (e.g., the wearable device 110 or the wearable device 162) worn by the human and configured to perform the blood pressure measurement.

Unlike the scheduled blood pressure measurement of the technique 530, the opportunistic blood pressure measurements are not required to be performed at a given time. A blood pressure measurement system (e.g., the system 100, the system 160, the system 200, or the system 250) implementing the technique 550 measures the blood pressure of the human when an activity condition is satisfied. The system may determine 556 the activity score based on sensor data (e.g., motion data from an accelerometer and/or heart rate data from a photoplethysmogram sensor) collected during a recent period (e.g., the last 5 minutes). For example, the activity score may be determined 556 as described in relation to operation 536 of FIG. 5C. An estimate of heart rate for the human may also be determined 538. For example, the estimate of heart rate may be determined 558 as described in relation to operation 538 of FIG. 5C.

If (at operation 559) the activity score and the estimate of heart rate both indicate that the human is still and at peace and ready to have their blood pressure measured, the measurement continues 560. For example, the technique 570 of FIG. 5D may be implemented to continue 560 the blood pressure measurement procedure. In some implementations, a blood pressure measurement is initiated responsive at least in part to the activity score satisfying a condition (e.g., that the activity score exceeds a threshold). In some implementations, a blood pressure measurement is initiated responsive at least in part to the estimated heart rate satisfying a condition (e.g., that the estimate of heart rate is below a threshold). Otherwise (at operation 559), the next wakeup time may be determined 562 based on the activity data. For example, a sliding window approach may be used to estimate a time in the future that the activity score might reach a threshold required to continue 560 the blood pressure measurement.

Figure 5D:
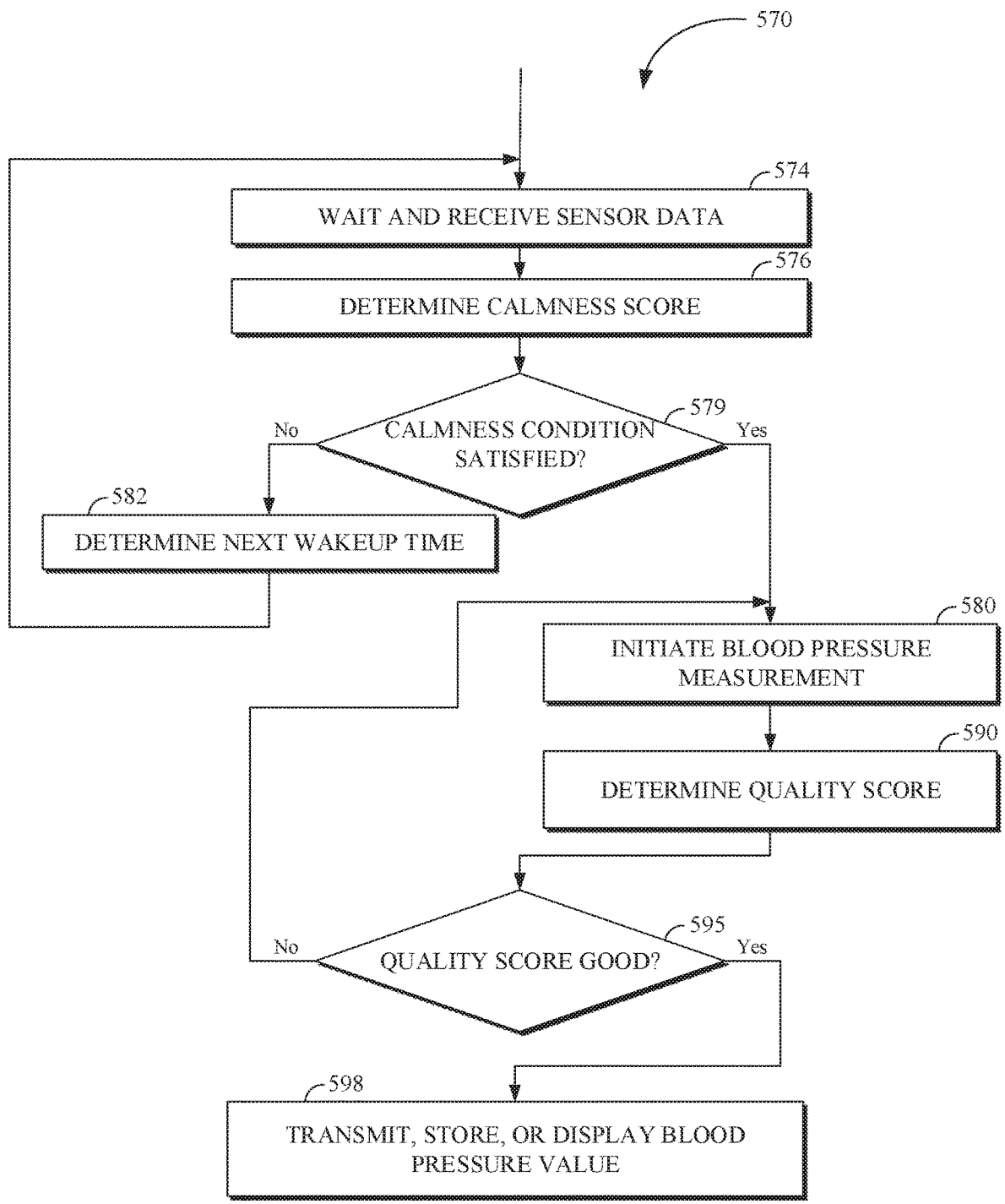
FIG. 5D is a flowchart of an example technique for checking a calmness score to time a blood pressure measurement.

FIG. 5D is a flowchart of an example technique 570 for checking a calmness score to time a blood pressure measurement. The example technique 570 includes waiting and receiving 574 sensor data and determining 576 a calmness score based on the sensor data. If (at operation 579) a calmness condition for the human is satisfied, then a blood pressure measurement pressure measurement is initiated 580. Otherwise (at operation 579), a next wakeup time is determined 582 and the procedure is restarted by waiting for and receiving 574 sensor data. The example technique 570 includes determining 590 a quality score for the initiated 580 blood pressure measurement. If (at operation 595) the quality score is good (e.g., the quality score exceeds a threshold), then a blood pressure value resulting from the initiated 580 blood pressure measurement is transmitted, stored, or displayed 598. Otherwise (at operation 595), a new blood pressure measurement is initiated 580, until a good quality score is achieved or the blood pressure measurement procedure times out and resets. For example, the technique 570 may be implemented by a processing apparatus (e.g., the processing apparatuses 310, 340, and 370) that is incorporated in or (directly or indirectly) in communication with a wearable device (e.g., the wearable device 110 or the wearable device 162) worn by the human and configured to perform the blood pressure measurement.

In some implementations, before the blood pressure measurement is initiated 580, a system (e.g., the system 100, the system 160, the system 200, or the system 250) implementing the technique 570 instructs the user to sit down, wear one or more cuffs (e.g., the blood pressure measurement cuff 130 and the GSR cuff 140), and stay calm. The system may collect GSR data for a period (e.g., 5 minutes) (at operation 574) and determine 576 a calmness score based on the GSR data. If (at operation 579) the calmness score indicates that the user has been calm during the period (e.g., the last 5 minutes), the system initiates 580 a blood pressure measurement for the human wearing the cuffs. Otherwise (at operation 579), it determines 582 the next wakeup time and wait until the user is ready for a blood pressure measurement. When the system is measuring the blood pressure of the human, the system also collects (at operation 574) accelerometer, photoplethysmogram sensor, GSR sensor, and cuff pressure data. The system may determine 590 a blood pressure quality score using the sensor data collected during the measurement. If (at operation 595) the score is good, the system stores 598 the measured blood pressure and the quality score to the phone. Otherwise (at operation 595), the system initiates another blood pressure measurement.

The example technique 570 includes receiving 574 sensor data including galvanic skin response data from the galvanic skin response sensor. In some implementations, the received 574 sensor data also includes heart rate data (e.g., data from a photoplethysmogram sensor or an electrocardiogram sensor). For example, sensor data may be received 574 via conductors that connect a sensor (e.g., the GSR cuff 140 or the heart rate sensor(s) 178) to a processing apparatus (e.g., the processing apparatus 310). For example, sensor data may be received 574 via wireless communications (e.g., using Bluetooth, ZigBee, or WiFi protocols) from a wearable device (e.g., the wearable device 110 or the wearable device 162) to a processing apparatus (e.g., the processing apparatus 340). For example, sensor data may be received 574 by a processing apparatus (e.g., the processing apparatus 370) via network communications (e.g., using IPv4 or IPv6 protocols) through a network interface (e.g., the network interface 376). For example, the received 574 sensor data may be raw sensor readings or they may be partially processed sensor readings (e.g., readings that have been filtered to suppress noise components in a signal).

The example technique 570 includes determining 576 a calmness score for the human based on the galvanic skin response data. For example, a calmness score may be determined 576 for the human based on the galvanic skin response data corresponding to a galvanic skin response signal within a sliding window of time. For example, the calmness score may be determined 576 by counting weighted peaks in GSR time series data. Mental agitation, or a lack of calm, may cause activation the sympathetic nervous systems (SNS) of a human, which induces sweat secretion and registers peaks in skin conductance of the human. These peaks may be detected and analyzed to determine 576 the calmness score. For example, the technique 600 of FIG. 6 may be used to determine the calmness score. In some implementations, a calmness score is mapped (e.g., by applying a non-linear mapping to a statistic of the galvanic skin response data) into a range (e.g., from 0 to 100) for combination with another score (e.g., an activity score). For example, the calmness score may reflect or be correlated with a mental state of the human is conducive or not to diagnostically useful blood pressure measurement.

In some implementations, responsive at least in part to the calmness score satisfying a condition (at operation 579), a blood pressure measurement is initiated 580 (e.g., using the blood pressure measurement cuff 130). Blood pressure data for the human that results from the blood pressure measurement may be received and a blood pressure value (e.g., a systolic blood pressure and/or a diastolic blood pressure) may be determined based on the blood pressure data.

The example technique 570 includes determining 590 a quality score for the blood pressure measurement. For example, the quality score may be determined 590 based on accelerometer, photoplethysmogram, galvanic skin response, and cuff pressure data. The system may compute a rate of changes in the acceleration to detect if the human moved during a blood pressure measurement. In implementations using a photoplethysmogram sensor, the system may compute heart rate changes before the blood pressure measurement. In some implementations, the system may evaluate the cuff pressure data quality to determine if the cuff is correctly worn on the human's fingers or wrist. In some implementations, the quality score may be determined 590 as a weighted average of individual scores from each sensor. For example, the quality score may be determined 590 based on a weighted average of an activity score and a calmness score. For example, the quality score may be determined 590 based on a weighted average of an activity score, a calmness score, and a pressure cuff placement score. The pressure cuff placement score may be based on analysis (e.g., to detect characteristic noise artifacts of a pressure cuff moving during a blood pressure measurement) of raw pressure reading from a blood pressure sensor and may indicate the extent to which a cuff was not properly placed or securely fastened during a blood pressure measurement.

The example technique 570 includes transmitting, storing, or displaying 598 a blood pressure value resulting from the initiated 580 blood pressure measurement that has satisfactory quality score. For example, the blood pressure value may be transmitted, stored, or displayed 598 along with the corresponding quality score. For example, the quality score may be transmitted 598, along with the blood pressure value, via a communications interface (e.g., the wireless interface 318, the wireless interface 348, the network interface 346, or the network interface 376) of a processing apparatus implementing the technique 570. For example, the quality score may be stored 598, along with the blood pressure value, in memory (e.g., the memory 314, the memory 344, or the memory 374) of a processing apparatus implementing the technique 570. For example, the quality score may be displayed 598, along with the blood pressure value, in a user interface (e.g., the user interface 320 or the user interface 350) of a processing apparatus implementing the technique 570.

Figure 6:
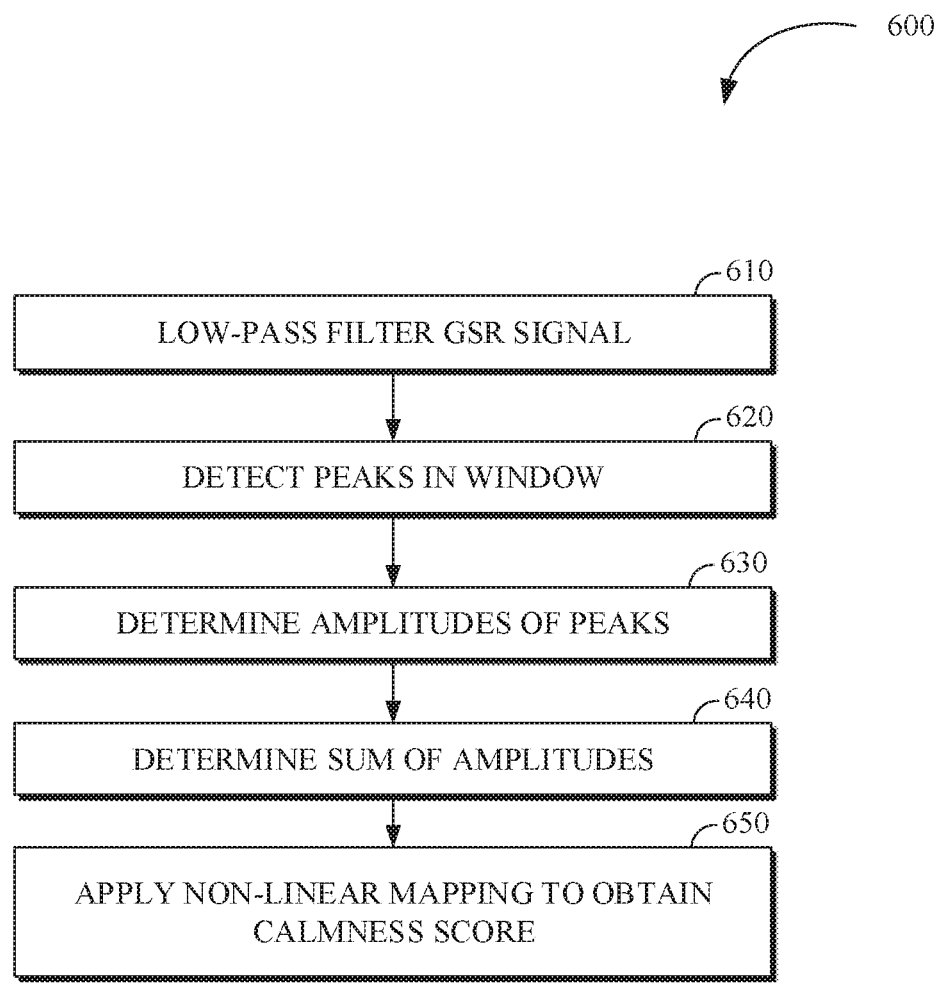
FIG. 6 is a flowchart of an example technique for determining a calmness score.

FIG. 6 is a flowchart of an example technique 600 for determining a calmness score. The technique 600 includes low-pass filtering 610 a GSR (galvanic skin response) signal; detecting 620 peaks within a time window of the GSR signal; determining 630 amplitudes of the peaks; determining 640 a sum of the amplitudes of the peaks; and applying 650 a non-linear mapping to the sum to obtain a calmness score. For example, the technique 600 may be implemented by a processing apparatus (e.g., the processing apparatuses 310, 340, and 370) that is incorporated in or (directly or indirectly) in communication with a wearable device (e.g., the wearable device 110 or the wearable device 162) worn by the human and configured to perform the blood pressure measurement. In some implementations, the technique 600 may be applied repeatedly or continuously while the wearable device is worn by the human to monitor a calmness prerequisite for high quality blood pressure measurements and opportunistically perform blood pressure measurements when conditions are good, which may provide a greater number of high quality blood pressure measurements for the human and enhance health tracking and medical diagnosis of the human.

The example technique 600 includes low-pas filtering 610 a GSR signal embodied in galvanic skin response data from a galvanic skin response sensor that is fastened to a human wearing a wearable device (e.g., the wearable device 110 or the wearable device 162). The low-pass filtering may be applied 610 to suppress high frequency noise in the GSR signal. In some implementations, an applied 610 low-pass filter may include a windowing function (e.g., a Hamming window or a generalized higher order cosine window) that selects a time window of the GSR signal.

The example technique 600 includes detecting 620 peaks in a galvanic skin response signal reflected in the galvanic skin response data. For example, peaks may be detected 620 in the galvanic skin response signal within a sliding window of time. For example, peaks may be detected based on zero crossing in a derivative or difference signal derived from the GSR signal and possibly with comparison to a minimum threshold for the GSR signal level.

The example technique 600 includes determining 630 amplitudes of the detected peaks and determining 640 a sum of the amplitudes of the detected peaks. For example, amplitudes determined 630 may be normalized peak amplitudes.

The example technique 600 includes applying 650 a non-linear mapping to a number based on the sum of the amplitudes of the detected peaks in the GSR signal to obtain a calmness score. For example, the calmness score may be determined based on a non-linear mapping of a sum of the amplitudes of the detected peaks. For example, the non-linear mapping may output calmness scores in the range of 0 to 100, where 100 is the calmest value (e.g., most conducive to medically useful blood pressure measurements.

Figure 7:
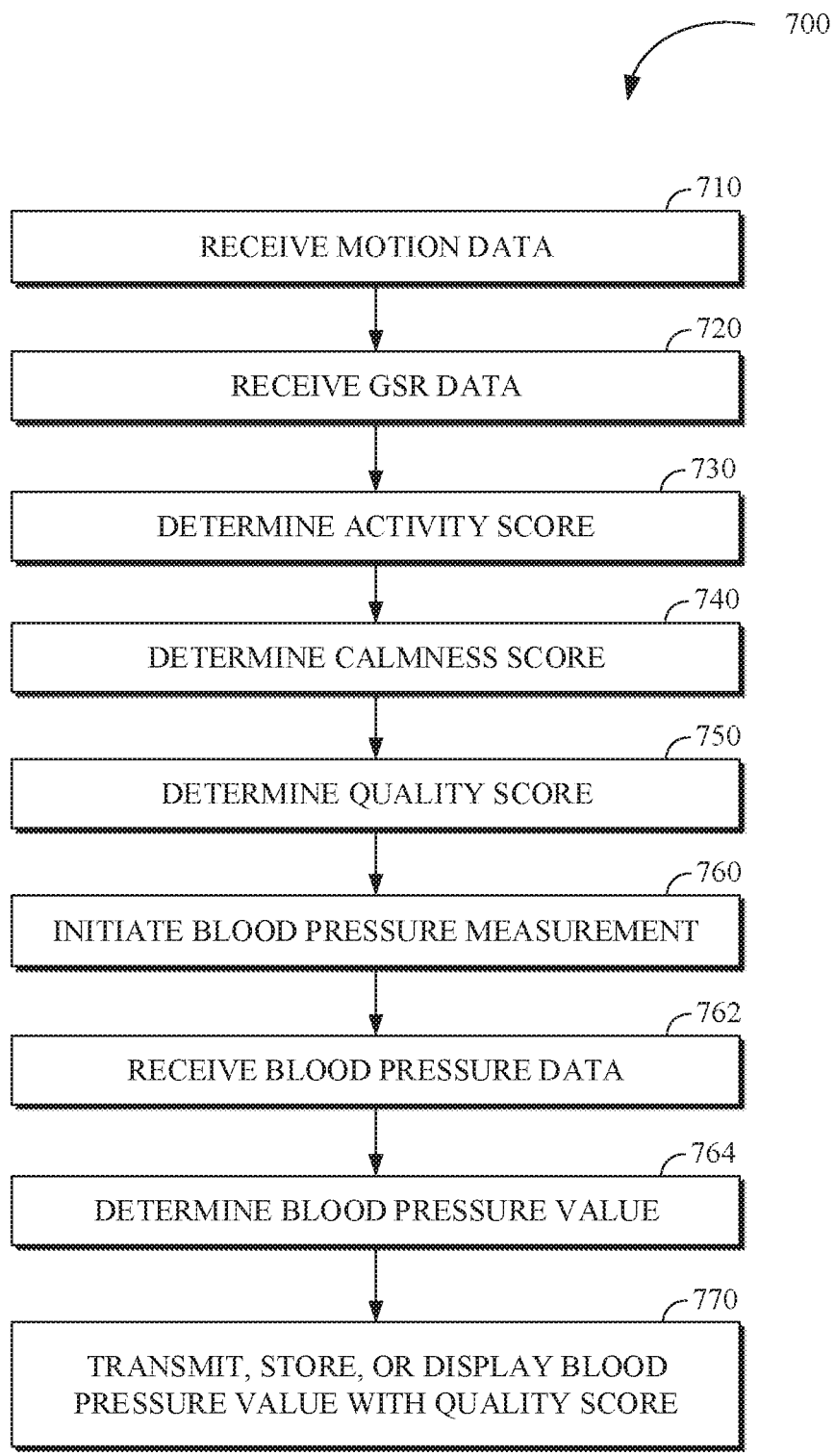
FIG. 7 is a flowchart of an example technique for blood pressure measurement with a quality score.

FIG. 7 is a flowchart of an example technique 700 for blood pressure measurement with a quality score. The technique 700 includes receiving 710 motion data from motion sensor worn by a human; receiving 720 GSR (galvanic skin response) data from a galvanic skin response sensor worn by the human; determining 730 an activity score based on the motion data; determining 740 a calmness score based on the GSR data; determining 750 a quality score based on the activity score and the calmness score; initiating 760 a blood pressure measurement using a blood pressure measurement cuff worn by the human; receiving 762 blood pressure data; determining 764 a blood pressure value based on the blood pressure data; and transmitting, storing, or displaying 770 the quality score along with the blood pressure value. For example, the technique 700 may be implemented by a processing apparatus (e.g., the processing apparatuses 310, 340, and 370) that is incorporated in or (directly or indirectly) in communication with a wearable device (e.g., the wearable device 110 or the wearable device 162) worn by the human and configured to perform the blood pressure measurement. In some implementations, the technique 700 may facilitate quality control for blood pressure measurements by allowing a user (e.g., the human or a health care provider) to select or weight useful blood pressure measurements later based on the quality scores for analysis and/or medical diagnosis.

The example technique 700 includes receiving 710 motion data from a motion sensor (e.g., an accelerometer and/or a gyroscope) that is attached to a device worn by the human. For example, the motion sensor may be attached to a band (e.g., the band 112 or the band 164) that is worn by the human. For example, the motion sensor may part of a personal computing device (e.g., the personal computing device 150 or the personal computing device 180) that is carried and/or in a pocket of clothing worn by the human. For example, motion data may be received 710 via conductors that connect a motion sensor (e.g., the motion sensor(s) 176 to a processing apparatus (e.g., the processing apparatus 310). For example, motion data may be received 710 via wireless communications (e.g., using Bluetooth, ZigBee, or WiFi protocols) from a wearable device (e.g., the wearable device 110 or the wearable device 162) to a processing apparatus (e.g., the processing apparatus 340). For example, the motion data may be received 710 by a processing apparatus (e.g., the processing apparatus 370) via network communications (e.g., using IPv4 or IPv6 protocols) through a network interface (e.g., the network interface 376). The received 710 motion data may be raw measurements or they may be partially processed measurements (e.g., measurements that have been filtered to suppress noise components in a signal). The motion data may be generated and received 710 at a time proximal to (e.g., just before, during, or just after) the blood pressure measurement initiated at operation 760.

The example technique 700 includes receiving 720 GSR (galvanic skin response) data from a galvanic skin response sensor. The galvanic skin response sensor may include two electrodes fastened to a hand of a human. For example, galvanic skin response data may be received 720 via conductors that connect a GSR cuff (e.g., the GSR cuff 140), which includes an electrode fastened to a finger of the human, to a processing apparatus (e.g., the processing apparatus 310). For example, galvanic skin response data may be received 720 via wireless communications (e.g., using Bluetooth, ZigBee, or WiFi protocols) from a wearable device (e.g., the wearable device 110 or the wearable device 162), which includes two or more electrodes fastened to the human, to a processing apparatus (e.g., the processing apparatus 340). For example, galvanic skin response data may be received 720 by a processing apparatus (e.g., the processing apparatus 370) via network communications (e.g., using IPv4 or IPv6 protocols) through a network interface (e.g., the network interface 376). The received 720 galvanic skin response data may be raw measurements or they may be partially processed measurements (e.g., measurements that have been filtered to suppress noise components in a signal). The GSR data may be generated and received 720 at a time temporally proximal to (e.g., just before, during, or just after) the blood pressure measurement initiated at operation 760.

The example technique 700 includes determining 730 an activity score based on the motion data. For example, the activity score may be determined 730 based on a Metabolic Equivalent of Task (MET) algorithm. Readings from one or more motion sensors (e.g., accelerometers and/or gyroscopes) on wearable device (e.g., a smartwatch) and/or on a personal computing device (e.g., a smartphone) may be used to infer a recent energy expenditure by a human wearing or carrying the motion sensor(s). The MET may be determined based on the human's energy expenditure during a recent period (e.g., the last 5 minutes) and the human's body weight. In some implementations, lower METs are associated with higher activity scores, such that a high activity score may be indicative of readiness for a diagnostically useful blood pressure measurement. For example, the activity score may be inversely proportional to the MET. The determination of the activity score at a time temporally proximal to a blood pressure measurement may be indicative of the quality of the blood pressure measurement.

The example technique 700 includes determining 740 a calmness score for the human based on the galvanic skin response data. For example, a calmness score may be determined 740 for the human based on the galvanic skin response data corresponding to a galvanic skin response signal within a sliding window of time. For example, the calmness score may be determined 740 by counting weighted peaks in GSR time series data. Mental agitation, or a lack of calm, may cause activation the sympathetic nervous systems (SNS) of a human, which induces sweat secretion and registers peaks in skin conductance of the human. These peaks may be detected and analyzed to determine 740 the calmness score. For example, the technique 600 of FIG. 6 may be used to determine the calmness score. In some implementations, a calmness score is mapped (e.g., by applying a non-linear mapping to a statistic of the GSR data) into a range (e.g., from 0 to 100) for combination with another score (e.g., an activity score). For example, the calmness score may reflect or be correlated with a mental state of the human is conducive or not to diagnostically useful blood pressure measurement.

The example technique 700 includes determining 750 a quality score based on the activity score and the calmness score. For example, the quality score may be determined 750 based at least in part on the calmness score. For example, the quality score may be determined 750 based at least in part on the activity score. In some implementations, the quality score is determined 750 based on a sum (e.g., a weighted sum) of the activity score and the calmness score. In some implementations, the quality score is determined 750 based on a product of the activity score and the calmness score.

The quality score may measure the extent to which the blood pressure is correctly measured or is useful for medical diagnosis. In some implementations, the range of the quality score is from 0 to 1 where 1 corresponds to high degree of confidence in the accuracy and usefulness of a corresponding blood pressure measurement, and 0 corresponds to a low degree of confidence in the accuracy and usefulness of a corresponding blood pressure measurement. For example, the quality score may indicate how likely the blood pressure measurement is correctly measured for medical diagnostic purposes. Ideally, the system makes accurate blood pressure measurements when the user is stationary, does not move their arms, and keeps calm during the measurement. The quality score may have a motion component to measure the impact of the cuff movement and a mood component to measure the human's mood on BP measurement accuracy. In some implementations, both components have the same range and/or meaning as the quality score. For example, a probabilistic model may be used to combine the two components as input to determine 750 the quality score. For example, the motion component of the quality score may be computed based on motion data from a motion sensor (e.g., an accelerometer and/or a gyroscope) of a wearable device ( ) worn by the human during the blood pressure measurement. A motion intensity value may be computed first and then the intensity value may be mapped to the motion component value from 0 to 1. The mapping may be learned using machine learning techniques. For example, the mood component may be computed as the calmness score mapped to the range of 0 to 1. Optionally, machine learning techniques may be applied to fine-tune the mood component.

The example technique 700 includes initiating 760 a blood pressure measurement using a blood pressure measurement cuff worn by the human. For example, the blood pressure measurement may be initiated 760 by sending a command to blood pressure cuff. For example, the processing apparatus 310 may initiate 760 a blood pressure measurement by sending a command via the sensor interface 316. For example, the processing apparatus 340 may initiate 760 a blood pressure measurement by sending a command via the wireless interface 348 through a wireless communications link with a wearable device that includes the blood pressure cuff. For example, the processing apparatus 370 may initiate 760 a blood pressure measurement by sending a command via the network interface 376 through a communications link with a wearable device that includes the blood pressure cuff. For example, the processing apparatus 166 may initiate 760 a blood pressure measurement by sending a command via the blood pressure controller 174 to the blood pressure cuff 172.

The example technique 700 includes receiving 762 blood pressure data for the human that results from the blood pressure measurement. For example, blood pressure data may be received 762 via conductors that connect a blood pressure measurement cuff (e.g., the blood pressure measurement cuff 130) to a processing apparatus (e.g., the processing apparatus 310). For example, the blood pressure data may be received 762 via wireless communications (e.g., using Bluetooth, ZigBee, or WiFi protocols) from a wearable device (e.g., the wearable device 110 or the wearable device 162) to a processing apparatus (e.g., the processing apparatus 340). For example, blood pressure data may be received 762 by a processing apparatus (e.g., the processing apparatus 370) via network communications (e.g., using IPv4 or IPv6 protocols) through a network interface (e.g., the network interface 376). The received 762 blood pressure data may be a sequence of raw pressure readings (e.g., in units of millimeters of mercury) or they may be partially processed (e.g., readings that have been filtered to suppress noise components in a signal). In some implementations, the received 762 blood pressure data may be a systolic blood pressure value and/or a diastolic blood pressure value.

The example technique 700 includes determining 764 a blood pressure value that is based on the blood pressure data. For example, oscillometric methods may be used to determine 764 a blood pressure value (e.g., a systolic and/or diastolic blood pressure value) based on a sequence of pressure readings from the blood pressure measurement cuff. In some implementations, the analysis to determine an estimate of a blood pressure of the human based on raw sensor readings may have been performed upstream (e.g., by the blood pressure controller 174 and/or the processing apparatus 166) before the blood pressure data was received 762 by an apparatus implementing the technique 700. For example, determining 764 the blood pressure value may be simply parsing and reading a blood pressure value from the blood pressure data.

The example technique 700 includes transmitting, storing, or displaying 770 the quality score in a manner such that the quality score is associated with the blood pressure value. For example, the quality score may be transmitted 770, along with the blood pressure value, via a communications interface (e.g., the wireless interface 318, the wireless interface 348, the network interface 346, or the network interface 376) of a processing apparatus implementing the technique 700. For example, the quality score may be stored 770, along with the blood pressure value, in memory (e.g., the memory 314, the memory 344, or the memory 374) of a processing apparatus implementing the technique 700. For example, the quality score and the blood pressure value may be associated by a pointer or a record in a database. For example, the quality score may be displayed 770, along with the blood pressure value, in a user interface (e.g., the user interface 320 or the user interface 350) of a processing apparatus implementing the technique 700.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A system, comprising:
   a band configured to be worn on a wrist of a human;
   a wireless communications interface attached to the band;
   a blood pressure measurement cuff integrated into the band;
   a galvanic skin response sensor, comprising two electrodes that are configured to be worn on a hand of the human, in which the galvanic skin response sensor is attached to the band;
   a pair of detachable finger cuffs that are connected to a cuff interface of the system, the pair of detachable finger cuffs comprising a first finger cuff including a first electrode of the two electrodes of the galvanic response sensor so that the first electrode is fastened to a first finger by the first finger cuff and a second finger cuff including a second electrode of the two electrodes of the galvanic response sensor so that the second electrode is fastened to a second finger by the second finger cuff;
   a motion sensor, attached to the band, to determine an activity score; and
   a processing apparatus configured to:
      monitor galvanic skin response data from the galvanic skin response sensor to determine a time to initiate a blood pressure measurement;
      at the determined time, initiate the blood pressure measurement using the blood pressure measurement cuff;
      receive motion data from the motion sensor;
      evaluate an intensity of physical activity, in a past time window, of the human from the motion data;
      determine the activity score for the human based upon the evaluation of the intensity of physical activity in the past time window from the motion data; and
      determine a calmness score for the human based on the galvanic skin response;
      determining an upcoming time to initiate the blood pressure measurement based on satisfying the activity score and the calmness core and
   wherein the blood pressure measurement is initiated based upon the calmness score and the activity score to determine blood pressure of the human;
   wherein the processing apparatus determines a quality score based upon the activity score and the calmness score to provide a degree of confidence of the blood pressure of the human; and
   wherein the system comprises a smartwatch.

2. The system of claim 1, wherein the processing apparatus is further configured to:
   determine the calmness score data by:
      detected peaks in a galvanic skin response signal reflected in the galvanic skin response data;
      determining amplitudes of the detected peaks; and
      determining the calmness score based on a non-linear mapping of a sum of the amplitudes of the detected peaks;
   receive the galvanic skin response data from the galvanic skin response sensor;
   receive blood pressure data for the human that results from the blood pressure measurement; and
   store a blood pressure value that is based on the blood pressure data.

3. The system of claim 2, wherein motion data is received from the motion sensor by the processor;
   and the processor determines an activity score based on the motion data.

4. The system of claim 2, further comprising a heart rate sensor, and in which the processing apparatus is further configured to:
   receive heart rate data from the heart rate sensor;
   determine an estimated heart rate based on the heart rate data; and
   in which the blood pressure measurement is initiated responsive at least in part to the estimated heart rate satisfying a condition.

5. The system of claim 2, in which the processing apparatus is attached to the band and the recent level of exertion is an expenditure during the last 5 minutes.

6. The system of claim 1, wherein the processing apparatus is further configured to:
   receive the galvanic skin response data from the galvanic skin response sensor;
   determine a calmness score for a human based on the galvanic skin response data;
   initiate the blood pressure measurement using the blood pressure measurement cuff;
   receive blood pressure data for the human that results from the blood pressure measurement;
   determine a blood pressure value that is based on the blood pressure data;
   determine a quality score based at least in part on the calmness score; and
   store the quality score along with the blood pressure value.

7. A method comprising:
   receiving galvanic skin response data from a galvanic skin response sensor that includes two electrodes fastened to a hand of a human;

monitoring the galvanic skin response data to determine a time for initiating a blood pressure measurement using a blood pressure measurement cuff worn by the human;
determining a calmness score for the human based on the galvanic skin response data;
reading motion data from one or more motion sensors;
evaluating an intensity of physical activity of the human from the motion data;
determining a recent level of exertion by the human;
determining an activity score for a recent period window from the motion data, the recent level of exertion, and the intensity of the human, wherein the recent period window is a sliding window of time;
determining an upcoming time to initiate the blood pressure measurement based on satisfying the activity score and the calmness score;
at the determined time, initiating the blood pressure measurement using the blood pressure measurement cuff based at least in part upon the calmness score and the activity score;
receiving blood pressure data for the human that results from the blood pressure measurement;
storing a blood pressure value that is based on the blood pressure data; and
determining a quality score based on the activity score and the calmness score so that a degree of confidence in the blood pressure measurement is provided.

8. The method of claim 7, wherein the calmness score is determined by:
detecting peaks in a galvanic skin response signal reflected in the galvanic skin response data;
determining amplitudes of the detected peaks; and
determining a calmness score based on a non-linear mapping of a sum of the amplitudes of the detected peaks; and
wherein monitoring the galvanic skin response data to determine the time comprises:
determining the calmness score for the human based on the galvanic skin response data corresponding to a galvanic skin response signal within a sliding window of time; and
comparing the calmness score to a first threshold to assess a first condition.

9. The method of claim 7, further comprising:
receiving motion data from a motion sensor that is attached to a device worn by the human; and
monitoring the motion data to determine the time for initiating a blood pressure measurement using a blood pressure measurement cuff worn by the human.

10. The method of claim 9, in which monitoring the motion data to determine the time comprises:
comparing the activity score to a second threshold to assess a second condition; and
responsive at least in part to the activity score satisfying the second condition, determining the time to be a current time or an upcoming time.

11. The method of claim 7, further comprising:
determining an estimate of heart rate for the human based on sensor data from at least one of the sensors from a group including a photoplethysmogram sensor and an electrocardiogram sensor, where the at least one sensors are worn by the human;
comparing the estimate of heart rate to a third threshold to assess a third condition; and
responsive at least in part to the estimate of heart rate satisfying the third condition, determining the time to be a current or upcoming time.

12. The method of claim 7, further comprising:
wherein the motion sensor is attached to a device worn by the human; and
storing the quality score in a manner such that the quality score is associated with the blood pressure value.

13. A system comprising:
a band configured to be worn on a wrist of a human;
a battery attached to the band;
a wireless communications interface attached to the band;
a blood pressure measurement cuff configured to be worn on the wrist or a finger of the human, in which the blood pressure measurement cuff is attached to the band;
a pair of galvanic skin response sensors detachably attached to the band and configured to connect to two fingers of the human in which the blood pressure measurement cuff is attached;
a motion sensor; and
a processing apparatus that is configured to:
monitor galvanic skin response data from the pair of galvanic skin response sensors;
determine a calmness score for the human based on the galvanic skin response data;
evaluate an intensity of physical activity from an immediately past five minutes;
compute an activity score for the human based upon data from the motion sensor sensing the human's energy expenditure and the intensity of the physical activity from the immediately past five minutes and the human's body weight,
map the activity score for comparison with a heart rate;
schedule an upcoming measurement via a user interface at a determined time based upon the calmness core and the activity score;
at the determined time, initiate the blood pressure measurement using the blood pressure measurement cuff based upon at least in part a condition of the calmness score and the activity score;
receive blood pressure data for the human that results from the blood pressure measurement; and
store a blood pressure value that is based on the blood pressure data.

14. The system of claim 1, wherein the activity score is determined based upon a Metabolic Equivalent of Task (MET) by using one or more motion sensors of the system to infer a recent energy expenditure by the human wearing or carrying the motion sensor and confirming a low MET score, within a sliding window, before a blood pressure measurement is taken.

15. The method of claim 7, wherein the calmness score has a scale from 0 to 100, where 100 corresponds to a claim state that is conducive to a blood pressure measurement and a score of 0 corresponds to an extremely agitated mental state that could impair a diagnosis based on a blood pressure measurement.

16. The system of claim 13, wherein the band is an inflatable watch band that is the blood pressure measurement cuff worn on the wrist; and
wherein the activity score is determined based upon a Metabolic Equivalent of Task (MET) by using data from the one or more motion sensors.

17. The method of claim 7, further comprising estimating a heart rate in part based upon the activity score or the calmness score, and determining a time to take the blood pressure measurement based in part on the heart rate estimate.

18. The system of claim 1, wherein the calmness score is determined in part based upon a pressure cuff placement score.

19. The system of claim 13, further comprising a communication interface that is configured to communicate a quality score, a display, and memory that is configured to store the quality score; wherein the processor correlates and stores the quality score along with a corresponding blood pressure value so that the quality score and the corresponding blood pressure is displayable in the display.

* * * * *